US007393544B2

(12) United States Patent
Dellamary et al.

(10) Patent No.: US 7,393,544 B2
(45) Date of Patent: Jul. 1, 2008

(54) DISPERSION FOR PULMONARY DELIVERY OF A BIOACTIVE AGENT

(75) Inventors: Luis A. Dellamary, San Marcos, CA (US); Thomas E. Tarara, San Diego, CA (US); Alexey Kabalnov, Corvallis, OR (US); Jeffry G. Weers, San Diego, CA (US); Ernest G. Schutt, San Diego, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 11/675,073

(22) Filed: Feb. 14, 2007

(65) Prior Publication Data

US 2007/0212405 A1 Sep. 13, 2007

Related U.S. Application Data

(63) Continuation of application No. 09/999,071, filed on Dec. 3, 2001, now Pat. No. 7,205,343, which is a continuation of application No. 09/218,209, filed on Dec. 22, 1998, now Pat. No. 6,433,040, which is a continuation of application No. PCT/US98/20613, filed on Sep. 29, 1998, which is a continuation-in-part of application No. 09/133,848, filed on Aug. 14, 1998, now abandoned, which is a continuation-in-part of application No. 09/106,932, filed on Jun. 29, 1998, now abandoned.

(60) Provisional application No. 60/060,337, filed on Sep. 29, 1997.

(51) Int. Cl.
*A61K 9/127* (2006.01)

(52) U.S. Cl. ........................... 424/450; 424/43; 424/45; 424/46; 424/426; 424/434; 424/435; 424/487; 424/489; 424/490

(58) Field of Classification Search .................. 424/43, 424/45, 46, 426, 434, 435, 450, 487, 489–490; 524/43, 45, 46, 426, 434, 435, 450, 487, 524/489, 490
See application file for complete search history.

(56) References Cited

U.S. PATENT DOCUMENTS

| | | | |
|---|---|---|---|
| 3,014,844 | A | 12/1961 | Thiel et al. |
| 4,590,206 | A | 5/1986 | Forrester et al. |
| 4,818,542 | A | 4/1989 | DeLuca et al. |
| 4,904,479 | A | 2/1990 | Illum |
| 5,011,678 | A | 4/1991 | Wang et al. |
| 5,069,936 | A | 12/1991 | Yen |
| 5,118,494 | A | 6/1992 | Schultz et al. |
| 5,126,123 | A | 6/1992 | Johnson |
| 5,173,298 | A | 12/1992 | Meadows |
| 5,182,097 | A | 1/1993 | Byron et al. |
| 5,190,029 | A | 3/1993 | Byron et al. |
| 5,208,226 | A | 5/1993 | Palmer |
| 5,225,183 | A | 7/1993 | Purewal et al. |
| 5,230,884 | A | 7/1993 | Evans et al. |
| 5,254,330 | A | 10/1993 | Ganderton et al. |
| 5,260,306 | A | 11/1993 | Boardman et al. |
| 5,284,656 | A | 2/1994 | Platz et al. |
| 5,299,566 | A | 4/1994 | Davis et al. |
| 5,308,620 | A | 5/1994 | Yen |
| 5,348,730 | A | 9/1994 | Greenleaf et al. |
| 5,376,359 | A | 12/1994 | Johnson |
| 5,437,272 | A | 8/1995 | Fuhrman |
| 5,470,885 | A | 11/1995 | Fuhrman et al. |
| 5,474,759 | A | 12/1995 | Fassberg et al. |
| 5,490,498 | A | 2/1996 | Faithfull et al. |
| 5,492,688 | A | 2/1996 | Byron et al. |
| 5,506,203 | A | 4/1996 | Backstrom et al. |
| 5,518,709 | A | 5/1996 | Sutton et al. |
| 5,518,731 | A | 5/1996 | Meadows |
| 5,518,998 | A | 5/1996 | Backstrom et al. |
| 5,547,656 | A | 8/1996 | Unger |
| 5,562,608 | A | 10/1996 | Sekins et al. |
| 5,569,450 | A | 10/1996 | Duan et al. |
| 5,580,575 | A | 12/1996 | Unger et al. |

(Continued)

FOREIGN PATENT DOCUMENTS

| | | |
|---|---|---|
| CA | 2036844 | 8/1991 |

(Continued)

OTHER PUBLICATIONS

Donna L. French et al., "The Influence of Formulation on Emission, Deaggregation and Deposition of Dry Powders for Inhalation," J. Aerosol Sci., vol. 27, No. 5, pp. 769-783 (1996).

(Continued)

*Primary Examiner*—Peter Szekely
(74) *Attorney, Agent, or Firm*—Guy Tucker; Naishadh Desai

(57) ABSTRACT

Stabilized dispersions are provided for the delivery of a bioactive agent. The dispersions preferably comprise a plurality of perforated microstructures dispersed in a suspension medium that typically comprises a liquid fluorochemical. As density variations between the suspended particles and suspension medium are minimized and attractive forces between microstructures are attenuated, the disclosed dispersions are particularly resistant to degradation, such as by settling or flocculation. In particularly preferred embodiments the stabilized dispersions may be directly administered to the lung of a patient using an endotracheal tube or bronchoscope.

21 Claims, 4 Drawing Sheets

U.S. PATENT DOCUMENTS

Figures 1, 1A:
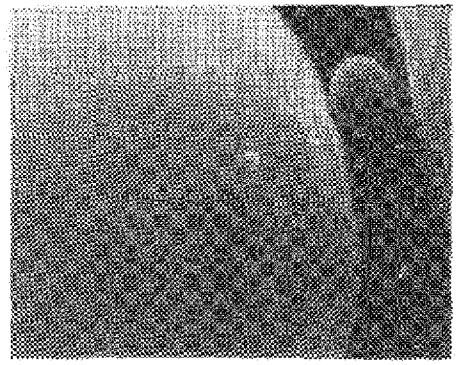

| | | | | |
|---|---|---|---|---|
| 5,605,673 | A | 2/1997 | Schutt et al. | |
| 5,605,674 | A | 2/1997 | Purewal et al. | |
| 5,612,053 | A | 3/1997 | Baichwal et al. | |
| 5,616,311 | A | 4/1997 | Yen | |
| 5,635,159 | A | 6/1997 | Fu Lu et al. | |
| 5,635,161 | A | 6/1997 | Adjei et al. | |
| 5,653,961 | A | 8/1997 | McNally et al. | |
| 5,653,962 | A | 8/1997 | Akehurst et al. | |
| 5,654,007 | A | 8/1997 | Johnson et al. | |
| 5,658,549 | A | 8/1997 | Akehurst et al. | |
| 5,667,809 | A | 9/1997 | Trevino et al. | |
| 5,674,471 | A | 10/1997 | Akehurst et al. | |
| 5,674,472 | A | 10/1997 | Akehurst et al. | |
| 5,674,473 | A | 10/1997 | Purewal et al. | |
| 5,676,929 | A | 10/1997 | Akehurst et al. | |
| 5,681,545 | A | 10/1997 | Purewal et al. | |
| 5,683,676 | A | 11/1997 | Akehurst et al. | |
| 5,683,677 | A | 11/1997 | Purewal et al. | |
| 5,688,782 | A | 11/1997 | Neale et al. | |
| 5,690,954 | A | 11/1997 | Illum | |
| 5,695,743 | A | 12/1997 | Purewal et al. | |
| 5,695,744 | A | 12/1997 | Neale et al. | |
| 5,707,352 | A | 1/1998 | Sekins et al. | |
| 5,718,222 | A | 2/1998 | Lloyd et al. | |
| 5,718,921 | A | 2/1998 | Mathiowitz et al. | |
| 5,720,940 | A | 2/1998 | Purewal et al. | |
| 5,724,957 | A | 3/1998 | Rubsamen et al. | |
| 5,725,841 | A | 3/1998 | Duan et al. | |
| 5,725,871 | A | 3/1998 | Illum | |
| 5,735,263 | A | 4/1998 | Rubsamen et al. | |
| 5,736,124 | A | 4/1998 | Akehurst et al. | |
| 5,741,478 | A | 4/1998 | Osborne et al. | |
| 5,741,522 | A | 4/1998 | Violante et al. | |
| 5,743,250 | A | 4/1998 | Gonda et al. | |
| 5,743,252 | A | 4/1998 | Rubsamen et al. | |
| 5,744,123 | A | 4/1998 | Akehurst et al. | |
| 5,744,166 | A | 4/1998 | Illum | |
| 5,747,445 | A | 5/1998 | Backstrom et al. | |
| 5,755,218 | A | 5/1998 | Johansson et al. | |
| 5,756,104 | A | 5/1998 | de Haan et al. | |
| 5,766,573 | A | 6/1998 | Purewal et al. | |
| 5,770,187 | A | 6/1998 | Hasebe et al. | |
| 5,770,222 | A | 6/1998 | Unger et al. | |
| 5,770,559 | A | 6/1998 | Manning et al. | |
| 5,770,585 | A | 6/1998 | Kaufman et al. | |
| 5,804,212 | A | 9/1998 | Illum | |
| 5,811,406 | A | 9/1998 | Szoka, Jr. et al. | |
| 5,814,607 | A | 9/1998 | Patton | |
| 5,817,293 | A | 10/1998 | Akehurst et al. | |
| 5,820,883 | A | 10/1998 | Tice et al. | |
| 5,829,435 | A | 11/1998 | Rivissamen et al. | |
| 5,830,430 | A | 11/1998 | Unger et al. | |
| 5,830,853 | A | 11/1998 | Backstrom et al. | |
| 5,855,913 | A | 1/1999 | Hanes et al. | |
| 5,856,367 | A | 1/1999 | Barrows et al. | |
| 5,858,784 | A | 1/1999 | Debs et al. | |
| 5,861,175 | A | 1/1999 | Walters et al. | |
| 5,863,554 | A | 1/1999 | Illum | |
| 5,874,063 | A | 2/1999 | Briggner et al. | |
| 5,874,064 | A | 2/1999 | Edwards et al. | |
| 5,891,844 | A | 4/1999 | Hafner | |
| 5,898,028 | A | 4/1999 | Jensen et al. | |
| 6,309,623 | B1 * | 10/2001 | Weers et al. | 424/455 |
| 6,565,885 | B1 * | 5/2003 | Tarara et al. | 424/489 |
| 6,630,169 | B1 * | 10/2003 | Bot et al. | 424/489 |
| 6,638,495 | B2 * | 10/2003 | Weers et al. | 424/45 |
| 6,946,117 | B1 * | 9/2005 | Schutt et al. | 424/45 |

FOREIGN PATENT DOCUMENTS

| | | |
|---|---|---|
| CA | 2136704 | 5/1995 |
| EP | 0274431 | 7/1988 |
| EP | 0372777 | 1/1993 |
| EP | 0391896 | 3/1994 |
| EP | 0536204 | 4/1994 |
| EP | 0611567 | 8/1994 |
| EP | 0553298 | 11/1994 |
| EP | 0653205 | 5/1995 |
| EP | 0655237 | 5/1995 |
| EP | 0656206 | 6/1995 |
| EP | 0658101 | 6/1995 |
| EP | 0513127 | 7/1995 |
| EP | 0493437 | 8/1995 |
| EP | 0556256 | 8/1995 |
| EP | 0616525 | 9/1995 |
| EP | 0499344 | 10/1995 |
| EP | 0587790 | 1/1996 |
| EP | 0605578 | 1/1996 |
| EP | 0588897 | 2/1996 |
| EP | 0536235 | 1/1997 |
| EP | 0539522 | 12/1998 |
| WO | WO 9104011 | 4/1991 |
| WO | WO 9111173 | 8/1991 |
| WO | WO 9112823 | 9/1991 |
| WO | WO 9200107 | 1/1992 |
| WO | WO 9211050 | 7/1992 |
| WO | WO 9214444 | 9/1992 |
| WO | WO 9218164 | 10/1992 |
| WO | WO 9311744 | 6/1993 |
| WO | WO 9311745 | 6/1993 |
| WO | WO 9314172 | 7/1993 |
| WO | WO 9408627 | 4/1994 |
| WO | WO 9500128 | 1/1995 |
| WO | WO 9505194 | 2/1995 |
| WO | WO 9515118 | 6/1995 |
| WO | WO 9517195 | 6/1995 |
| WO | WO 9523613 | 9/1995 |
| WO | WO 9524892 | 9/1995 |
| WO | WO 9527476 | 10/1995 |
| WO | WO 9531182 | 11/1995 |
| WO | WO 9531964 | 11/1995 |
| WO | WO 9609814 | 4/1996 |
| WO | WO 9615814 | 5/1996 |
| WO | WO 9618388 | 6/1996 |
| WO | WO 9619197 | 6/1996 |
| WO | WO 9619198 | 6/1996 |
| WO | WO 9619199 | 6/1996 |
| WO | WO 9619968 | 7/1996 |
| WO | WO 9626746 | 9/1996 |
| WO | WO 9632149 | 10/1996 |
| WO | WO 9640068 | 12/1996 |
| WO | WO 9703649 | 2/1997 |
| WO | WO 9735562 | 10/1997 |
| WO | WO 9736574 | 10/1997 |
| WO | WO 9736578 | 10/1997 |
| WO | WO 9740819 | 11/1997 |
| WO | WO 9741833 | 11/1997 |
| WO | WO 9744012 | 11/1997 |
| WO | WO 9744013 | 11/1997 |
| WO | WO 9800111 | 1/1998 |
| WO | WO 9801161 | 1/1998 |
| WO | WO 9805302 | 2/1998 |
| WO | WO 9808519 | 3/1998 |
| WO | WO 9813031 | 4/1998 |
| WO | WO 9816205 | 4/1998 |
| WO | WO 9817257 | 4/1998 |
| WO | WO 9829097 | 7/1998 |
| WO | WO 9829098 | 7/1998 |
| WO | WO 9829099 | 7/1998 |
| WO | WO 9829140 | 7/1998 |
| WO | WO 9830207 | 7/1998 |

| | | |
|---|---|---|
| WO | WO 9831346 | 7/1998 |
| WO | WO 9833480 | 8/1998 |
| WO | WO 9833487 | 8/1998 |
| WO | WO 9841188 | 9/1998 |
| WO | WO 9906026 | 2/1999 |

OTHER PUBLICATIONS

Lwandiko E. Masinde et al., "Aerosolized Aqueous Suspensions of Poly(L-lactic Acid) Microspheres," 100 International J. of Pharmaceutics, pp. 123-131 (1993).

* cited by examiner

PFC/PC = 0

PFC/PC = 1.1

PFC/PC = 2.2

Figures 1, 1A, 2:
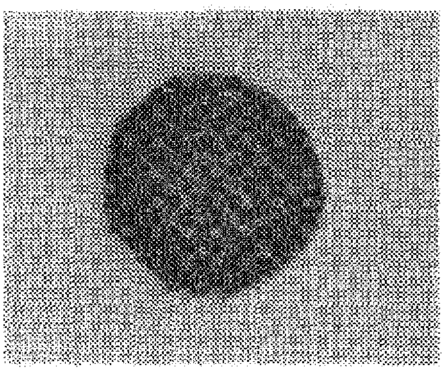
Figures 1, 1B:
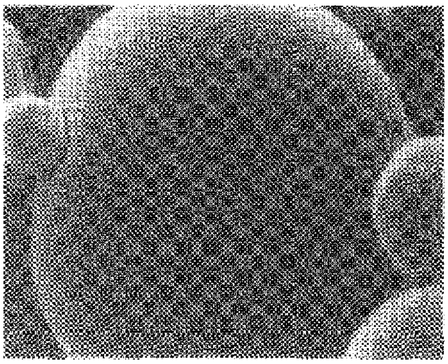
Figures 1, 1B, 2:
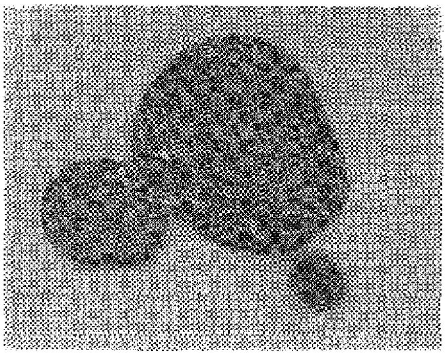
Figures 1, 1C:
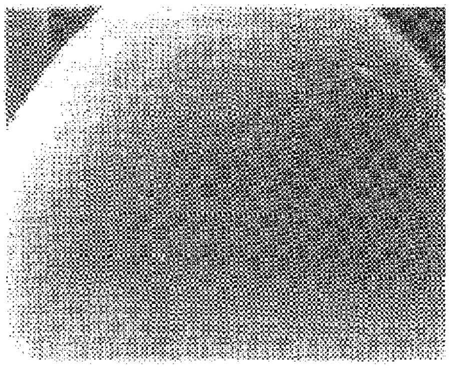
Figures 1, 1C, 2:
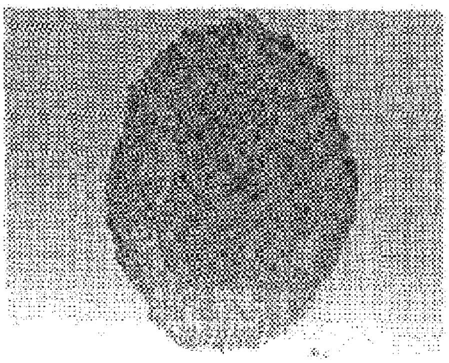
Figure 2:
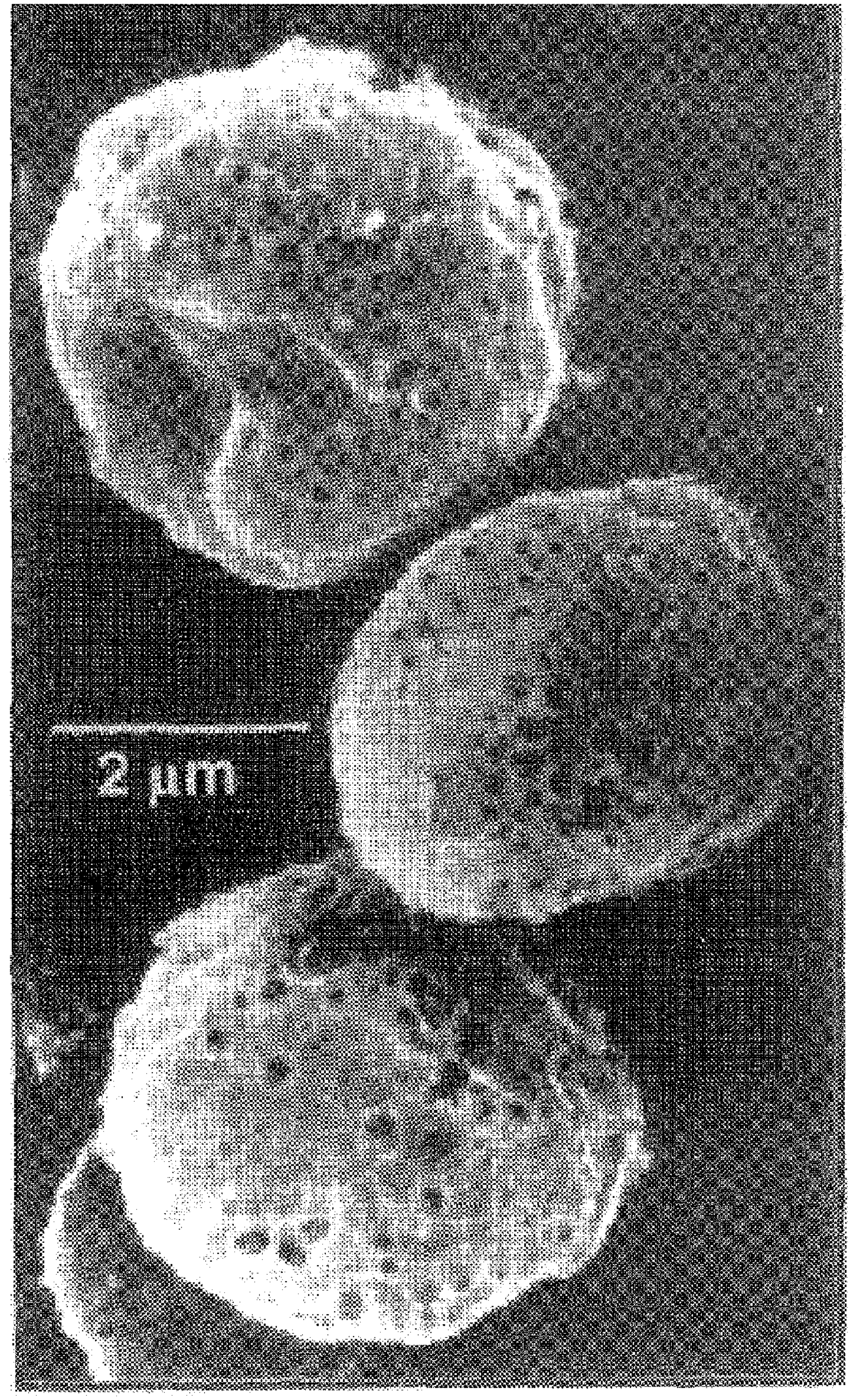
Figure 3A:
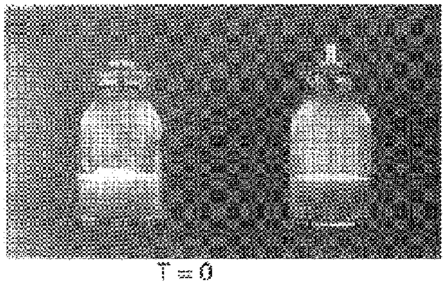
Figure 3B:
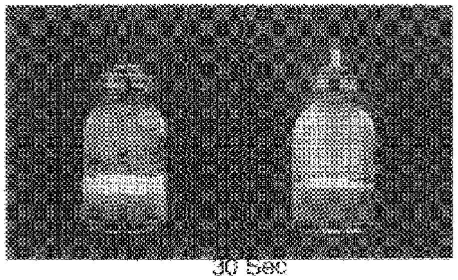
Figure 3C:
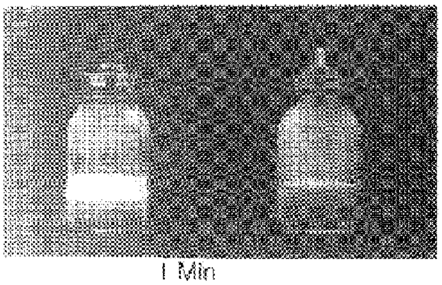
Figure 3D:
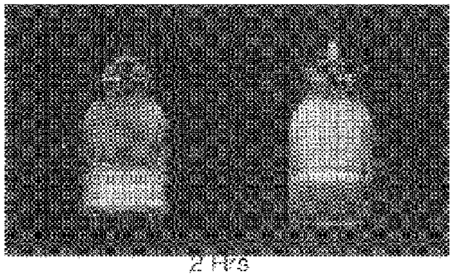

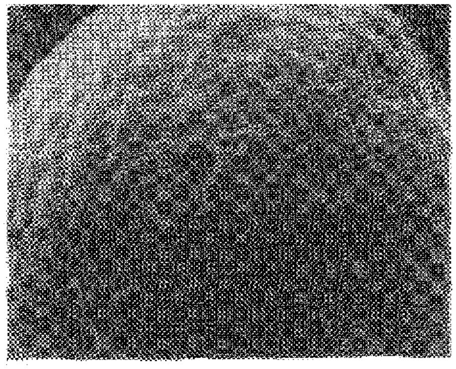
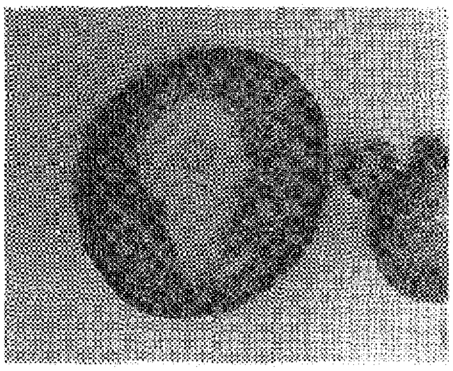
FIG. 1D-1 PFC/PC = 4.8 FIG. 1D-2
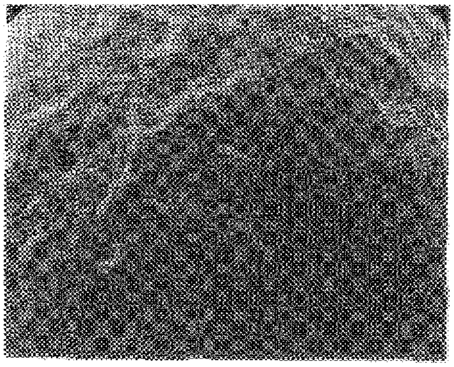
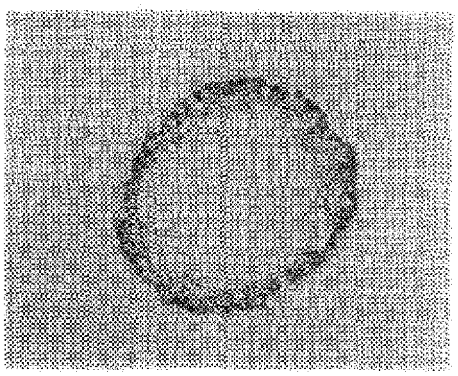
FIG. 1E-1 PFC/PC = 18.8 FIG. 1E-2
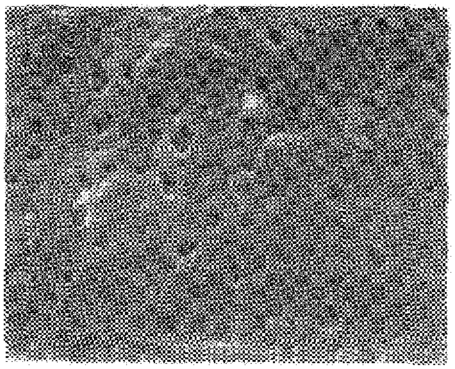
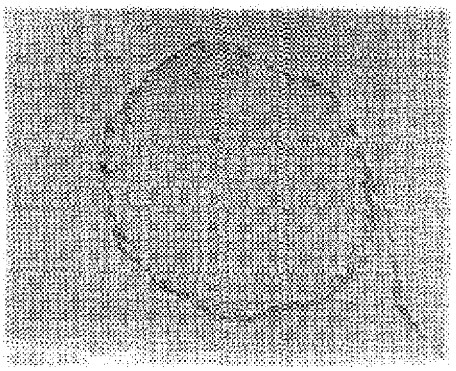
FIG. 1F-1 PFC/PC = 44.7 FIG. 1F-2

T = 0

30 Sec

1 Min

2 Hrs

DISPERSION FOR PULMONARY DELIVERY OF A BIOACTIVE AGENT

CROSS REFERENCE

The present application is a continuation of U.S. application Ser. No. 09/999,071 filed Dec. 3, 2001, now U.S. Pat. No. 7,205,343 which is a continuation of U.S. application No. 09/218,209 U.S. Pat. No. 6,433,040 filed Dec. 22, 1998, which is a continuation of PCT/U.S.99/20613 filed Sep. 29, 1998, which is a continuation-in-part of U.S. patent application Ser. No. 09/133,848 filed Aug. 14, 1998, now abandoned, which is a continuation-in-part of U.S. patent application Ser. No. 09/106,932 filed Jun. 29, 1998, now abandoned, which claims priority from U.S. Provisional Application Ser. No. 60/060,337 filed Sep. 29, 1997 and now lapsed. All of these applications are now incorporated by reference herein in their entireties.

BACKGROUND

Embodiments of the present invention relate to compositions, systems, and methods, for the pulmonary delivery to a patient, of microstructures in a suspension medium.

The efficacy of many pharmaceutical agents is predicated on their ability to proceed to the selected target sites and remain there in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes that are subject to repeated drainage or flushing as part of the body's natural physiological functions offer significant impediments to the effective administration of pharmaceutical agents. In this respect, delivery and retention problems are often encountered when administering compounds through the respiratory or gastrointestinal tracts. Repeated administration of fairly large doses are often required to compensate for the amount of drug washed away and to maintain an effective dosing regimen when employing such routes. Moreover, the molecular properties of the pharmaceutical compound may impair the absorption through a given delivery route, thereby resulting in a substantial reduction in efficacy. For instance, insoluble particulates are known to be subject to phagocytosis and pinocytosis, resulting in the accelerated removal of the compound from the target site. Such reductions in delivery and retention time complicate dosing regimes, waste pharmaceutical resources and generally reduce the overall efficacy of the administered drug.

In this respect, one class of delivery vehicles that has shown great promise when used for the administration of pharmaceutical agents is fluorochemicals. During recent years, fluorochemicals have found wide ranging application in the medical field as therapeutic and diagnostic agents. The use of fluorochemicals to treat medical conditions is based, to a large extent, on the unique physical and chemical properties of these substances. In particular, the relatively low reactivity of fluorochemicals allows them to be combined with a wide variety of compounds without altering the properties of the incorporated agent. This relative inactivity, when coupled with other beneficial characteristics such as an ability to carry substantial amounts of oxygen, radioopaqueness for certain forms of radiation and low surface energies, have made fluorochemicals invaluable for a number of therapeutic and diagnostic applications.

Among these applications is liquid ventilation. For all practical purposes, liquid ventilation became a viable technique when it was discovered that fluorochemicals could be used as the respiratory promoter. Liquid breathing using oxygenated fluorochemicals has been explored for some time. For example, an animal submerged in an oxygenated fluorochemical liquid, may exchange oxygen and carbon dioxide normally when the lungs fill with the fluorochemical. In this regard it has been shown that mammals can derive adequate oxygen for survival when submerged by breathing the oxygenated fluorochemical liquid. In particular, it has been established that total liquid ventilation may keep mammals alive for extended periods prior to returning them to conventional gas breathing.

Those skilled in the art will appreciate that contemporary liquid ventilation is an alternative to standard mechanical ventilation which involves introducing an oxygenatable liquid medium into the pulmonary air passages for the purposes of waste gas exchange and oxygenation. Essentially, there are two separate techniques for performing liquid ventilation, total liquid ventilation and partial liquid ventilation. Total liquid ventilation or "TLV" is the pulmonary introduction of warmed, extracorporeally oxygenated liquid respiratory promoter (typically fluorochemicals) at a volume greater than the functional residual capacity of the subject. The subject is then connected to a liquid breathing system and tidal liquid volumes are delivered at a frequency depending on respiratory requirements while exhaled liquid is purged of $CO_2$ and oxygenated extracorporeally between the breaths. This often involves the use of specialized fluid handling equipment.

Conversely, partial liquid ventilation or "PLV" involves the use of conventional mechanical ventilation in combination with pulmonary administration of a respiratory promoter capable of oxygenation. In PLV a liquid, vaporous or gaseous respiratory promoter (i.e. a fluorochemical) is introduced into the pulmonary air passages at volumes ranging from just enough to interact with or coat a portion of the pulmonary surface all the way up to the functional residual capacity of the subject. Respiratory gas exchange may then be maintained for the duration of the procedure by, for example, continuous positive pressure ventilation using a conventional open-circuit gas ventilator; Alternatively, gas exchange may be maintained through spontaneous respiration. When the procedure is over, the introduced respiratory promoter or fluorochemical may be allowed to evaporate from the lung rather than being physically removed as in TLV. For the purposes of the instant application the term "liquid ventilation" will be used in a generic sense and shall be defined as the introduction of any amount of respiratory promoter or fluorochemical into the lung, including the techniques of partial liquid ventilation, total liquid ventilation and liquid dose installation.

Use of liquid ventilation may provide significant medical benefits that are not available through the use of conventional mechanical ventilators employing a breathable gas. For example, the weight of the respiratory promoter opens alveoli with much lower ventilator pressure than is possible with gas. Additionally, liquid ventilation using fluorochemicals as the respiratory promoter has been shown to be effective in rinsing out congestive materials associated with respiratory distress syndrome. Moreover, liquid ventilation has been shown to be a promising therapy for the treatment of respiratory distress syndromes involving surfactant deficiency or dysfunction. Elevated alveolar surface tension plays a central role in the pathophysiology of the Respiratory Distress Syndrome (RDS) in premature infants and is thought to contribute to the dysfunction in children and adults. Liquid ventilation, particularly using fluorochemicals, is effective in surfactant-deficient disorders because it eliminates the air/fluid interfaces in the lung and thereby greatly reduces pulmonary surface tension. Moreover, liquid ventilation can be accomplished without undue alveolar pressures or impairing cardiac output and provides excellent gas exchange even in premature infants. Finally, fluorochemicals have also been shown to have pulmonary and systemic anti-inflammatory effects.

In addition to liquid ventilation, it has been recognized that fluorochemicals may be effective in the pulmonary delivery of bioactive agents in the form of liquid or solid particulates. For example, pulmonary delivery of bioactive agents using fluorochemical suspensions is described in Sekins et al., U.S. Pat. No. 5,562,608, Fuhrman, U.S. Pat. No. 5,437,272, Faithful et al. U.S. Pat. No. 5,490,498, Trevino et al. U.S. Pat. No. 5,667,809 and Schutt U.S. Pat. No. 5,540,225 each of which is incorporated herein by reference. The bioactive agents may preferably be delivered in conjunction with partial liquid ventilation or lavage. Due to the physical characteristics of compatible respiratory promoters or fluorochemicals, the use of such techniques provides for improved dispersion of the incorporated agent in the lung thereby increasing uptake and increasing efficacy. Further, direct administration of the bioactive agent is particularly effective in the treatment of lung disease as poor vascular circulation of diseased portions of the lung reduces the efficacy of intravenous drug delivery. Besides treating pulmonary disorders, fluorochemical pharmaceutical formulations administered to the lung could also prove useful in the treatment and/or diagnosis of disorders such as RDS, impaired pulmonary circulation, cystic fibrosis and lung cancer. It will also be appreciated that, in addition to the pulmonary route of administration, fluorochemicals could advantageously be used for the administration of compounds via other routes such as topical, oral (e.g. for administration to the gastrointestinal tract), intraperitoneal, or ocular. Unfortunately, regardless of the administration route, the use of fluorochemical suspensions may result in unreliable and irreproducible drug delivery due to the administration of a non-homogeneous dispersion or instability of the particulates in the fluorochemical phase.

More particularly, drug suspensions in liquid fluorochemicals comprise heterogeneous systems which usually require redispersion prior to use. Yet, because of factors such as patient compliance, obtaining a relatively homogeneous distribution of the pharmaceutical compound is not always easy or successful. In addition, prior art formulations comprising micronized particulates may be prone to aggregation of the particles which can result in inadequate delivery of the drug. Crystal growth of the suspensions via Ostwald ripening may also lead to particle size heterogeneity and can significantly reduce the shelf-life of the formulation. Another problem with conventional dispersions is particle coarsening. Coarsening may occur via several mechanisms such as flocculation, fusion, molecular diffusion, and coalescence. Over a relatively short period of time these processes can coarsen the formulation to the point where it is no longer usable. As such, while such systems are certainly a substantial improvement over prior art non-fluorochemical delivery vehicles, the drug suspensions may be improved upon to enable formulations with improved stability that also offer more efficient and accurate dosing at the desired site.

DRAWINGS

FIGS. 1A1 to 1F2 illustrate changes in particle morphology as a function of variation in the ratio of fluorocarbon blowing agent to phospholipid (PFC/PC) present in the spray dry feed. The micrographs, produced using scanning electron microscopy and transmission electron microscopy techniques, show that the absence of FCs, or at low PFC/PC ratios, the resulting spray dried microstructures comprising gentamicin sulfate are neither particularly hollow or porous. Conversely, at high PFC/PC ratios, the particles contain numerous pores and are substantially hollow with thin walls.

FIG. 2 is a scanning electron microscopy image of perforated microstructures comprising cromolyn sodium illustrating a preferred hollow/porous morphology.

FIGS. 3A to 3D are photographs illustrating the enhanced stability provided by the dispersions of the present invention over time as compared to a commercial cromolyn sodium formulation (Intal, Rhone-Poulenc-Rorer). In the photographs, the commercial formulation on the left rapidly separates while the dispersion on the right, formed in accordance with the teachings herein, remains stable over an extended period.

DESCRIPTION

While the present invention may be embodied in many different forms, disclosed herein are specific illustrative embodiments thereof that exemplify the principles of the invention. It should be emphasized that the present invention is not limited to the specific embodiments illustrated.

As set forth above, the present invention provides methods and compositions that allow for the formation of stabilized suspensions that may advantageously be used for the delivery of bioactive agents. The enhanced stability of the suspensions is primarily achieved by lowering the van der Waals attractive forces between the suspended particles, and by reducing the differences in density between the suspension medium and the particles. In accordance with the teachings herein, the increases in suspension stability may be imparted by engineering perforated microstructures that are then dispersed in a compatible suspension medium. In this regard, the perforated microstructures comprise pores, voids, and hollows, defects or other interstitial spaces that allow the fluid suspension medium to freely permeate or perfuse the particulate boundary. Particularly preferred embodiments comprise perforated microstructures that are hollow and porous, almost honeycombed or foam-like in appearance. In especially preferred embodiments the perforated microstructures comprise hollow, porous spray dried microspheres.

With respect to the instant specification, the terms "perforated microstructures" and "perforated microparticles" are used to describe porous products, preferably comprising a bioactive agent, distributed throughout the suspension medium in accordance with the teachings herein. Accordingly, the subject terms may be used interchangeably throughout the instant specification unless the contextual setting indicates otherwise.

When the perforated microstructures are placed in the suspension medium (i.e. propellant), the suspension medium is able to permeate the particles, thereby creating a "homodispersion", wherein both the continuous and dispersed phases are substantially indistinguishable. Since the defined or "virtual" particles (i.e. comprising the volume circumscribed by the microparticulate matrix) are made up almost entirely of the medium in which they are suspended, the forces driving particle aggregation (flocculation) are minimized. Additionally, having the microstructures filled with the medium, thereby effectively slowing particle creaming or sedimentation minimizes the differences in density between the defined particles and the continuous phase.

It should further be appreciated that the suspension medium may be any liquid or compound that is in liquid form, under appropriate thermodynamic conditions, for formation of a compatible particulate dispersion. Unless otherwise dictated by contextual restraints, the terms "suspension medium," "suspension media" and "nonaqueous continuous phase" are held to be equivalent for the purposes of the instant application and may be used interchangeably. For embodiments wherein the stabilized dispersion is to be used in conjunction liquid dose instillation, the suspension medium preferably comprises hydrocarbons or fluorocarbons having a vapor pressure less than about one atmosphere. That is, it will preferably be a liquid under standard conditions of one atmosphere and 25° C.

Due to their stability and substantially homogeneous nature, the stabilized suspensions of the present invention are compatible with inhalation therapies and may be used in conjunction with metered dose inhalers, dry powder inhalers and nebulizers. In particularly preferred embodiments the disclosed perforated microstructures may be dispersed in a suitable suspension medium (e.g. a long chain liquid fluorochemical) and directly administered to the pulmonary air passages of a patient in need thereof. For the purposes of the instant specification, methods comprising direct administration of a stabilized dispersion to the lungs such as through an endotracheal tube or a bronchoscope; will be termed liquid dose, instillation. While the compositions of the present invention are particularly effective for pulmonary drug delivery, it will be appreciated that they may also be used to drugs to a variety of physiological sites including body cavities and organs. Accordingly, the stabilized dispersions may be administered topically, subcutaneously intramuscularly, intraperitoneally, nasally, vaginally, rectally, orally or ocularly.

In contrast to many prior art suspensions, the dispersions of the present invention are designed not to increase repulsion between particles, but rather to decrease attractive forces. The principal forces driving flocculation in nonaqueous, media are van der Waals (VDW) attractive forces. VDW forces are quantum mechanical in origin, and can be visualized as attractions between fluctuating dipoles (i.e. induced dipole-induced dipole interactions). Dispersion forces are extremely short-range and scale as the sixth power of the distance between atoms. When two macroscopic bodies approach one another the dispersion attractions between the atoms sums up. The resulting force is of considerably longer range, and depends on the geometry of the interacting bodies.

More specifically, for two spherical particles, the magnitude of the VDW potential, $V_A$, can be approximated by the equation:

$$V_A=((-A_{eff})/(6H_0))*((R_1*R_2)/(R_1+R_2))$$

where $A_{eff}$ is the effective Hamaker constant which accounts for the nature of the particles and the medium, $H_0$ is the distance between particles, and $R_1$ and $R_2$ are the radii of spherical particles 1 and 2. The effective Hamaker constant is proportional to the difference in the polarizabilities of the dispersed particles and the suspension medium: $A_{eff}=(\sqrt{A_{SM}}-\sqrt{A_{PART}})^2$, where $A_{SM}$ and $A_{PART}$ are the Hamaker constants for the suspension medium and the particles, respectively. As the suspended particles and the dispersion medium become similar in nature, $A_{SM}$ and $A_{PART}$ become closer in magnitude, and $A_{eff}$ and $V_A$ become smaller. That is, by reducing the differences between the Hamaker constant associated with suspension medium and the Hamaker constant associated with the dispersed particles, the effective Hamaker constant (and corresponding van der Waals attractive forces) may be reduced.

One way to minimize the differences in the Hamaker constants is to create a "homodispersion", that is make both the continuous and dispersed phases essentially indistinguishable as discussed above. Besides exploiting the morphology of the particles to reduce the effective Hamaker constant, the components of the structural matrix (defining the perforated microstructures) will preferably be chosen so as to exhibit a Hamaker constant relatively close to that of the selected suspension medium. In this respect, one may use the actual values of the Hamaker constants of the suspension medium and the particulate components to determine the compatibility of the dispersion ingredients and provide a good indication as to the stability of the preparation. Alternatively, one could select relatively compatible perforated microstructure components and suspension mediums using characteristic physical values that coincide with measurable Hamaker constants but are more readily discernible.

In this respect, it has been found that the refractive index values of many compounds tend to scale with the corresponding Hamaker constant. Accordingly, easily measurable refractive index values may be used to provide a fairly good indication as to which combination of suspension medium and particle excipients will provide dispersion having a relatively low effective Hamaker constant and associated stability. It will be appreciated that, since refractive indices of compounds are widely available or easily derived, the use of such values allows for the formation of stabilized dispersions in accordance with the present invention without undue experimentation. For the purpose of illustration only, the refractive indices of several compounds compatible with the disclosed dispersions are provided in Table I immediately below:

TABLE I

| Compound | Refractive Index |
|---|---|
| HFA-134a | 1.172 |
| HFA-227 | 1.223 |
| CFC-12 | 1.287 |
| CFC-114 | 1.288 |
| PFOB | 1.305 |
| Mannitol | 1.333 |
| Ethanol | 1.361 |
| n-octane | 1.397 |
| DMPC | 1.43 |
| Pluronic F-68 | 1.43 |
| Sucrose | 1.538 |
| Hydroxyethylstarch | 1.54 |
| Sodium chloride | 1.544 |

Consistent with the compatible dispersion components set forth above, those skilled in the art will appreciate that the formation of dispersions wherein the components have a refractive index differential of less than about 0.5 is preferred. That is, the refractive index of the suspension medium will preferably be within about 0.5 of the refractive index associated with the perforated particles or microstructures. It will further be appreciated that the refractive index of the suspension medium and the particles may be measured directly or approximated using the refractive indices of the major component in each respective phase. For the perforated microstructures, the major component may be determined on a weight percent basis. For the suspension medium, the major component will typically be derived on a volume percentage basis. In selected embodiments of the present invention the refractive index differential value will preferably be less than about 0.45, about 0.4, about 0.35 or even less than about 0.3. Given that lower refractive index differentials imply greater dispersion stability, particularly preferred embodiments comprise index differentials of less than about 0.28, about 0.25, about 0.2, about 0.15 or even less than about 0.1. It is submitted that a skilled artisan will be able to determine which excipients are particularly compatible without undue experimentation given the instant disclosure. The ultimate choice of preferred excipients will also be influenced by other factors, including biocompatibility regulatory status, ease of manufacture and cost.

In contrast to prior art attempts to provide stabilized suspensions which require surfactants that are soluble in the suspension medium, the present invention provides for stabilized dispersions, at least in part, by immobilizing the bioactive agent(s) and excipients (including surfactants) within the structural matrix of the hollow, porous microstructures. Accordingly, preferred excipients useful in the present invention are substantially insoluble in the suspension medium. Under such conditions, even surfactants like, for example, lecithin cannot be considered to have surfactant properties in the present invention since surfactant performance requires the amphiphile to be reasonably soluble in the suspension medium. The use of insoluble excipients also reduces the potential for particle growth by Ostwald ripening.

As alluded to above, the minimization of density differences between the particles and the continuous phase is largely dependent on the perforated and/or hollow nature of the microstructures, such that the suspension medium constitutes most of the particle volume. As used herein, the term "particle volume" corresponds to the volume of suspension medium that would be displaced by the incorporated hollow/porous particles if they were solid, i.e. the volume defined by the particle boundary. For the purposes of explanation these fluid filled particulate volumes may be referred to as "virtual particles." Preferably the average volume of the bioactive agent/excipient shell or matrix (i.e. the volume of medium actually displaced by the perforated microstructure) comprises less than 70% of the average particle volume (or less than 70% of the virtual particle). More preferably, the volume of the microparticulate matrix comprises less than about 50%, 40%, and 30% or even 20% of the average particle volume. Even more preferably the average volume of the shell/matrix comprises less than about 10%, 5% or 3% of the average particle volume. Those skilled in the art will appreciate that such a matrix or shell volumes typically contributes little to the virtual particle density which is overwhelmingly dictated by the suspension medium found therein. Of course, in selected embodiments the excipients used to form the perforated microstructure may be chosen so the density of the resulting matrix or shell approximates the density of the surrounding suspension medium.

It will be appreciated that the use of such microstructures will allow the apparent density of the virtual particles to approach that of the suspension medium substantially eliminating the attractive van der Waals forces. Moreover, as previously discussed, the components of the microparticulate matrix are preferably selected, as much as possible given other considerations, to approximate the density of suspension medium. Accordingly, in preferred embodiments of the present invention the virtual particles and the suspension medium will have a density differential of less than about 0.6 $g/cm^3$. That is, the mean density of the virtual particles (as defined by the matrix boundary) will be within approximately 0.6 $g/cm^3$ of the suspension medium. More preferably, the mean density of the virtual particles will be within 0.5, 0.4, 0.3 or 0.2 $g/cm^3$ of the selected suspension medium. In even more preferable embodiments the density differential will be less than about 0.1, 0.05, 0.01, or even less than 0.005 $g/cm^3$.

In addition to the aforementioned advantages, the use of hollow, porous particles allows for the formation of free-flowing dispersions comprising much higher volume fractions of particles in suspension. It should be appreciated that the formulation of prior art dispersions at volume fractions approaching close-packing generally results in dramatic increases in dispersion viscoelastic behavior. Rheological behavior of this type is counterproductive in the administration of bioactive agents. Those skilled in the art will appreciate that, the volume fraction of the particles may be defined as, the ratio of the apparent volume of the particles (i.e. the particle volume), to the total volume of the system. Each system has a maximum volume fraction or packing fraction. For example, particles in a simple cubic arrangement reach a maximum packing fraction of 0.52 while those in a face centered cubic/hexagonal close packed configuration reach a maximum packing fraction of approximately 0.74. For non-spherical particles or polydisperse systems, the derived values are different. Accordingly, the maximum packing fraction is often considered to be an empirical parameter for a given system.

Here, it was surprisingly found that the porous structures of the present invention do not exhibit undesirable viscoelastic behavior even at high volume fractions, approaching close packing. To the contrary, they remain as free flowing, low viscosity suspensions having little or no yield stress when compared with analogous suspensions comprising solid particulates. The low viscosity of the disclosed suspensions is thought to be due, at least in large part, to the relatively low VDW attraction, between the fluid-filled hollow, porous particles. As such, in selected embodiments the volume fraction of the disclosed dispersions is greater than approximately 0.3. Other embodiments may have packing values on the order of 0.3 to about 0.5 or on the order of 0.5 to about 0.8, with the higher values approaching a close packing condition. Moreover, as particle sedimentation tends to naturally decrease when the volume fraction approaches close packing, the formation of relatively concentrated dispersions may further increase formulation stability.

Although the methods and compositions of the present invention may be used to form relatively concentrated suspensions the stabilizing factors work equally well at much lower packing volumes and such dispersions are contemplated as being within the scope of the instant disclosure. In this regard it will be appreciated that dispersions comprising low volume fractions are extremely difficult to stabilize using prior art techniques. Conversely, dispersions incorporating perforated microstructures comprising a bioactive agent as described herein are particularly stable even at low volume fractions. Accordingly, the present invention allows for stabilized dispersions, and particularly respiratory dispersions, to be formed and used at volume fractions less than 0.3. In some preferred embodiments the volume fraction is approximately 0.0001-0.3, more preferably 0.001-0.01. Yet other preferred embodiments comprise stabilized suspensions having volume fractions from approximately 0.01 to approximately 0.1.

The perforated microstructures of the present invention may also be used to stabilize dilute suspensions of micronized bioactive agents. In such embodiments the perforated microstructures may be added to increase the volume fraction of particles in the suspension, thereby increasing suspension stability to creaming or sedimentation. Further, in these embodiments the incorporated microstructures may also act in preventing close approach (aggregation) of the micronized drug particles. It should be appreciated that the perforated microstructures incorporated in such embodiments do not necessarily comprise a bioactive agent. Rather, they may be formed exclusively of various excipients, including surfactants.

As indicated throughout the instant specification the dispersions of the present invention are preferably stabilized. In a broad sense, the term “stabilized dispersion” will be held to mean any dispersion that resists aggregation, flocculation or creaming to the extent required to provide for the effective delivery of a bioactive agent. While those skilled in the art will appreciate that there are several methods that may be used to assess the stability of a given suspension, a preferred method for the purposes of the present invention comprises determination of creaming or sedimentation time. In this regard, the creaming time shall be defined as the time for the suspended drug particulates to cream to ½ the volume of the suspension medium. Similarly, the sedimentation time may be defined as the time it takes for the particulates to sediment in ½ the volume of the liquid medium. One relatively simple way to determine the creaming time of a preparation is to provide a particulate suspension is sealed glass vials. The vials are agitated or shaken to provide relatively homogeneous dispersions which are then set aside and observed: using appropriate instrumentation or by eye. The time necessary for the suspended particulates to cream to ½ the volume of the suspension medium (i.e. to rise to the top half of the suspension medium) or to sediment within ½ the volume (i.e. to settle in the bottom half of the medium) is then noted. Suspension formulations having a creaming time greater than 1 minute are preferred and indicates suitable stability. More preferably, the stabilized dispersions comprise creaming times of greater than about 2, 5, 10, 15, 20 or 30 minutes. In particularly preferred embodiments the stabilized dispersions exhibit creaming times of greater than about 1, 1.5, 2, 2.5, 3, 4 or even 5 hours. Substantially equivalent periods for sedimentation times are similarly indicative of compatible dispersions.

Regardless of the ultimate composition or precise creaming time, the stabilized respiratory dispersions of the present invention comprise a plurality of perforated microstructures or nicroparticulates that are dispersed or suspended in the suspension medium. Preferably the perforated microstructures comprise a structural matrix that exhibits, defines or comprises voids, pores, defects, hollows, spaces, interstitial spaces, apertures, perforations or holes that allows the surrounding suspension medium to freely permeate, fill or pervade the microstructure. The absolute shape (as opposed to the morphology) of the perforated microstructure is generally not critical and any overall configuration that provides the desired stabilization characteristics is contemplated as being within the scope of the invention. Accordingly, while preferred embodiments can comprise approximately microspherical shapes, collapsed, deformed or fractured particulates are also compatible. With this caveat, it will be appreciated that particularly preferred embodiments of the invention comprise spray dried hollow, porous ionospheres.

In order to maximize dispersion stability and optimize bioavailability upon administration; the mean geometric particle size of the perforated microstructures is preferably about 0.5-50 μm, more preferably 1-30 μm. Unlike aerosolization techniques, liquid dose instillation or administration of bioactive agents does not depend critically on the aerodynamic properties of the particle for efficient biodistribution. Rather, the unique wettability characteristics of the FC suspension medium and the homogeneous nature of the dispersion promotes efficient biodistribution. Thus, there may be some advantage to using larger particles (i.e. 5-30 μm) for this application, since recent studies (Edwards et al., Science 1997, 276:1868-1871, which is incorporated herein by reference) have suggested that large porous particles may be able to provide a sustained release of bioactive agent. Edwards et al. claim that their large porous particles are effective sustained release agents upon inhalation because they are too large to be effectively cleared by pulmonary macrophages, yet light enough to penetrate deep into the lung, thereby avoiding clearance by the mucociliary escalator. In this regard it will be appreciated that the compositions and methods of the present invention may provide for the deep lung deposition of the bioactive particulates thereby countering, at least in part, the mucociliary escalator. Accordingly, larger perforated microstructures having a geometric diameter of greater than approximately 5 μm may prove to be particularly effective when administered (i.e. by LDI using the disclosed dispersions.

Besides the aforementioned advantages, there may be significant differences in local versus systemic bioavailability depending upon the size of the hollow porous particles delivered via liquid dose instillation. For example it is easy to envision that smaller particles (ca. 1 μm) may be more efficiently delivered to the alveolus than large particles (ca. 20 μm). The choice of particle size will ultimately be dependent on the nature of the bioactive agent and its intended site of action. In especially preferred embodiments the perforated microstructures will comprise a powder of dry, hollow, porous microspherical shells of approximately 1 to 30 μm in diameter, with shell thicknesses of approximately 0.1 μm to approximately 0.5 μm. It is a particular advantage of the present invention that the particulate concentration of the dispersions and structural matrix components can be adjusted to optimize the delivery characteristics of the selected particle size.

As alluded to throughout the instant specification the porosity of the microstructures may play a significant part is establishing dispersion stability. In this respect, the mean porosity of the perforated microstructures may be determined through electron microscopy coupled with modern imaging techniques. More specifically, electron micrographs of representative samples of the perforated microstructures may be obtained and digitally analyzed to quantify the porosity of the preparation. Such methodology is well known in the art and may be undertaken without undue experimentation.

For the purposes of the present invention, the mean porosity (i.e. the percentage of the particle surface area that is open to the interior and/or a central void) of the perforated microstructures may range from approximately 0.5% to approximately 80%. In more preferred embodiments, the mean porosity will range from approximately 2% to approximately 40%. Based on selected production parameters, the mean porosity may be greater than approximately, 2%, 5%, 10%, 15%, 20%, 25% or 30% of the microstructure surface area. In other embodiments, the mean porosity of the microstructures may be greater than about 40%, 50%, 60%, 70% or even 80%. As to the pores themselves, they typically range in size from about 5 nm, to about 400 nm, with mean pore sizes preferably in the range of from about 20 nm, to about 200 nm. In particularly preferred embodiments the mean pore size will be in the range of from about 50 nm to about 100 nm.

Whatever configuration and/or size distribution is ultimately selected for the perforated microstructure, the composition of the defining structural matrix may comprise any one of a number of biocompatible materials. It will be appreciated that, as used herein, the terms “structural matrix” or "microstructure matrix" are equivalent and shall be held to mean any solid material forming the perforated microstructures which define a plurality of voids, apertures, hollows, defects, pores, holes, fissures, etc. that promote the formation of stabilized dispersions as explained above. The structural matrix may be soluble or insoluble in an aqueous environment. In preferred embodiments the perforated microstructure defined by the structural matrix comprises a spray dried hollow porous microsphere incorporating at least one surfactant. For other selected embodiments the particulate material may be coated one or more times with polymers, surfactants or other compounds which aid suspension.

More generally, the perforated microstructures may be formed of any biocompatible material that is relatively stable and preferably insoluble with respect to the selected suspension medium and can provide the necessary perforated configuration. While a wide variety of materials may be used to form the particles, in particularly preferred embodiments the structural matrix is associated with, or comprises, a surfactant such as phospholipid or fluorinated surfactant. Although not required, the incorporation of a compatible surfactant can improve the stability of the respiratory dispersions, increase pulmonary deposition and facilitate the preparation of the suspension. Moreover, by altering the components, the density of the structural matrix may be adjusted to approximate the density of the surrounding medium and further stabilize the dispersion. Finally, as will be discussed in further detail below, the perforated microstructures preferably comprise at least one bioactive agent.

As set forth above the perforated microstructures of the present invention may optionally be associated with, or comprise, one or more surfactants. Moreover, miscible surfactants may optionally be combined with the suspension medium liquid phase. It will be appreciated by those skilled in the art that the use of surfactants, while not necessary to practice the instant invention, may further increase dispersion stability, simplify formulation procedures or increase bioavailability upon administration. With respect to metered dose makers (MDIs) surfactants further serve to lubricate the metering valve, thereby ensuring consistent reproducibility of valve actuation and accuracy of dose dispersed. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

In a broad sense surfactants suitable for use in the present invention include any compound or composition that aids in the formation and maintenance of the stabilized respiratory dispersions by forming a layer at the interface between the structural matrix and the suspension medium. The surfactant may comprise a single compound or any combination of compounds, such as in the case of co-surfactants. Particularly preferred surfactants are substantially insoluble in the propellant, nonfluorinated, and selected from the group consisting of saturated and unsaturated lipids, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized preparations.

Lipids, including phospholipids, from both natural and synthetic sources are particularly compatible with the present invention and may be used in varying concentrations to form the structural matrix. Generally compatible lipids comprise those that have a gel to liquid crystal phase transition greater than about 40° C. Preferably the incorporated lipids are relatively long chain (i.e. $C_{16}$-$C_{22}$) saturated lipids and more preferably comprise phospholipids. Exemplary phospholipids useful in the disclosed stabilized preparations comprise egg phosphatidylcholine, dilauroylphosphatidylcholine, dioleylphosphatidylcholine, dipalmitoylphosphatidyl-choline, disteroylphosphatidylcholine, short-chain phosphatidylcholines, phosphatidylethanolamine, dioleylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (Spans® 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic® F-68), poloxamer 407 (Pluroni® F-127), and poloxamer 338. Ionic surfactants such as sodium sulfosuccinate, and fatty acid soaps may also be utilized. In preferred embodiments the microstructures may comprise oleic acid or its alkali salt.

In addition to the aforementioned surfactants, cationic surfactants or lipids are preferred especially in the case of delivery or RNA or DNA. Examples of suitable cationic lipids include: DOTMA, N-[1-(2,3-dioleyloxy)propyl]-N,N,N-trimethylammonium chloride; DOTAP, 1 ,2-dioleyloxy-3-(trirnethylammonio)propane; and DOTB, 1 ,2-dioleyl-3-(4'-trimethylammonio)butanoyl-sn-glycerol. Polycationic amino acids such as polylysine, and polyarginine are also contemplated.

Those skilled in the art will further appreciate that a wide range of surfactants may optionally be used in conjunction with the present invention. Moreover, the optimum surfactant or combination thereof for a given application can readily be determined by empirical studies that do not require undue experimentation. It will further be appreciated that the preferred insolubility of any incorporated surfactant in the suspension medium will dramatically decrease the associated surface activity. As such, it is arguable as to whether these materials have surfactant-like character prior to contracting an aqueous bioactive surface (e.g. the aqueous hypophase in the lung). Finally, as discussed in more detail below, surfactants comprising the porous particles may also be useful in the formation of precursor oil-in-water emulsions (i.e. spray drying feed stock) used during processing to form the structural matrix.

On a weight to weight basis, the structural matrix of the perforated microstructures may comprise relatively high levels of surfactant. In this regard, the perforated microstructures will preferably comprise greater than about 1%, 5%, 10%, 15%, 18%, or even 20% w/w surfactant. More preferably, the perforated microstructures will comprise greater than about 25%, 30%, 35%, 40%, 45%, or 50% w/w surfactant. Still other exemplary embodiments will comprise perforated microstructures wherein the surfactant or surfactants are present at greater than about 55%, 60%, 65%, 70%, 75%, 80%, 85%, 90% or even 95% w/w. In selected embodiments the perforated microstructures will comprise essentially 100% w/w of a surfactant such as a phospholipid. Those skilled in the art will appreciate that, in such cases, the balance of the structural matrix (where applicable) will preferably comprise a bioactive agent or non surface active excipients or additives.

While such surfactant levels are preferably employed in perforated microstructures, they may be used to provide stabilized systems comprising relatively nonporous, or substantially solid, particulates. That is, while preferred embodiments will comprise perforated microstructures or microspheres associated with high levels of surfactant, acceptable dispersions may be formed using relatively low porosity particulates of the same surfactant concentration (i.e. greater than about 10% or 20% w/w). In this respect such embodiments are specifically contemplated as being within the scope of the present invention.

In other preferred embodiments of the invention the structural matrix defining the perforated microstructure optionally comprises synthetic or natural polymers or combinations thereof In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by' selecting the appropriate polymers, the delivery profile of the respiratory dispersion may be tailored to optimize the effectiveness of the bioactive agent.

Besides the aforementioned polymer materials and surfactants it may be desirable to add other excipients to an aerosol formulation to improve microsphere rigidity, drug delivery and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the particulate matrix to provide structure and form to the perforated microstructures (i.e. microspheres). These excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like, disaccharides such as lactose, maltose, sucrose, trehalose, and the like; trisaccharides such as raffinose and the like; and other carbohydrates such as starches (hydroxyethylstarch), cyclodextrins and maltodextrins. Amino acids are also suitable excipients with glycine preferred. Mixtures of carbohydrates and amino acids are further held to be within the scope of the present invention. The inclusion of both inorganic (e.g. sodium chloride, calcium chloride), organic salts (e.g. sodium citrate, sodium ascorbate, magnesium gluconate, sodium gluconate, tromethamine hydrochloride) and buffers is also contemplated.

Yet other preferred embodiments include perforated microstructures that may comprise, or may be coated with, charged species that prolong residence time at the point of contact or enhance penetration through mucosae. For example, anionic charges are known to favor mucoadhesion, while cationic charges may be used to associate the formed microparticulate with negatively charged bioactive agents such as genetic material. The charges may be imparted though the association or incorporation of polyanionic or polycationic materials such as polyacrylic acids, polylysine, polylactic acid and chitosan.

In addition to, or instead of, the components discussed above, the perforated microstructures will preferably comprise at least one bioactive agent. As used herein, "bioactive agent" refers to a substance which is used in connection with an application that is therapeutic or diagnostic in nature, such as in methods for diagnosing the presence or absence of a disease in a patient and/or in methods for treating a disease in a patient. As to compatible bioactive agents, those skilled in the art will, appreciate that any therapeutic or diagnostic agent may be incorporated in the stabilized dispersions of the present invention. For example, the bioactive agent may be selected from the group consisting of antiallergics, bronchodilators, bronchoconstrictors, pulmonary lung surfactants, analgesics, antibiotics, leukotriene inhibitors or antagonists, anticholinergics, mast cell inhibitors, antihistamines, antiintlammatories, antineoplastics, anesthetics, anti-tuberculars, imaging agents, cardiovascular agents, enzymes, steroids, genetic material, viral vectors, antisense agents, proteins, peptides and combinations thereof. Particularly preferred bioactive agents comprise compounds which are to be administered systemically (i.e. to the systemic circulation of a patient) such as peptides, proteins or polynucleotides. As will be disclosed in more detail below, the bioactive agent may be incorporated, blended in, coated on or otherwise associated with the perforated microstructure. Particularly preferred bioactive agents for use in accordance with the invention include anti-allergics, peptides and proteins, bronchodilators and anti-inflammatory steroids for use in the treatment of respiratory disorders such as asthma by inhalation therapy. Yet another associated advantage of the present invention is the effective delivery of bioactive agents.

With respect to particulate dispersions, the selected bioactive agent, or agents, may be used as the sole structural component of the perforated microstructures. Conversely, the perforated microstructures may comprise one or more components (i.e. structural materials, surfactants, excipients, etc.) in addition to the incorporated bioactive agents. In particularly preferred embodiments, the suspended perforated microstructures will comprise relatively high concentrations of surfactant (greater than about 10% w/w) along with the incorporated bioactive agent(s). Finally, it should be appreciated that the particulate or perforated microstructure may be coated, linked or otherwise associated with the bioactive agent in a non-integral manner. Whatever configuration is selected, it will be appreciated that the associated bioactive agent may be used in its natural form, or as one or more salts known in the art.

It will be appreciated that the distributed particles or perforated microstructures of the present invention may exclusively comprise one or more bioactive agents (i.e. 100% w/w). However, in selected embodiments the particles or perforated microstructures may incorporate much less bioactive agent depending on the activity thereof. Accordingly, for highly active materials, the particles may incorporate as little as 0.001% by weight, although a concentration of greater than about 0.1% w/w is preferred. Other embodiments of the invention may comprise greater than about 5%, 10%, 15%, 20%, 25%, 30% or, even 40% w/w bioactive agent. Still more preferably the particles or perforated microstructures may comprise greater than about 50%, 60%, 70%, 75%, 80% or, even 90% w/w bioactive agent. In particularly preferred embodiments the final stabilized respiratory dispersion desirably contains from about 40%-60% w/w, more preferably 50%-70% w/w, and even more preferably 60%-90% w/w of bioactive agent relative to the weight of the microparticulate matrix or particulate. The precise amount of bioactive agent incorporated in the stabilized dispersions of the present invention is dependent upon the agent of choice, the volume of suspension media required to effectively distribute the drug, the required dose and the form of the drug actually used for incorporation. Those skilled in the art will appreciate that, such determinations may be made by using well known pharmacological techniques, in combination with the teachings of the present invention.

Accordingly, bioactive agents that are suitable for pulmonary administration in conjunction with the teachings herein include any drug that may be presented in a form which is relatively insoluble in the selected medium and subject to pulmonary uptake in physiologically effective amounts. Compatible bioactive agents may comprise hydrophilic and lipophilic respiratory agents, bronchodilators, pulmonary lung surfactants, antibiotics, antivirals, anti-inflammatories, steroids, antihistaminics, histamine antagonists, leukotriene inhibitors or antagonists, anticholinergics, antineoplastics, anesthetics, enzymes, lung surfactants, cardiovascular agents, genetic material including DNA and RNA, viral vectors, immunoactive agents, imaging agents, vaccines, immunosuppressive agents, peptides, proteins and combinations thereof. Particularly preferred bioactive agents, for localized administration include mast cell inhibitors (anti-allergics), bronchodilators, and anti-inflammatory steroids for use in the treatment of respiratory disorders such as asthma by inhalation therapy, i.e. cromoglycate (e.g. the sodium salt), and albuterol (e.g. the sulfate salt). For systemic delivery (e.g. for the treatment of autoimmune diseases such as diabetes or multiple sclerosis), peptides and proteins are particularly preferred.

Exemplary medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, tripedane, cortisone, prednisone, prednisilone, dexamethasone, betamethasone, or triamcinolone acetojnide; antitussives, e.g. noscapine; bronchodilators, e.g. ephedrine, adrenaline, fenoterol, formoterol, isoprenaline, metaproterenol, salbutamol, albuterol, salmeterol, terbutaline; diuretics, e.g. amiloride; anticholinergics, e.g. ipatropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, T-cell receptor agonists or antagonists, LHRH, nafarelin, goserelin, leuprolide, interferon, rhu IL-1 receptor, macrophage activation factors such as lymphokines and muramyl dipeptides, opioid peptides and neuropeptides such as enkaphalins, endorphins, renin inhibitors, cholecystokinins, growth hormones, leukotriene inhibitors, α-antitrypsin, and the like. In addition, bioactive agents that comprise an RNA or DNA sequence, particularly those useful for gene therapy, genetic vaccination, genetic tolerization or antisense applications, may be incorporated in the disclosed dispersions as described herein. Representative DNA plasmids include, but are not limited to pCMVβ (available from Genzyme Corp, Framington, Mass.) and pCMV-β-gal (a CMV promotor linked to the *E. coli* Lac-Z gene, which codes for the enzyme β-galactosidase).

With respect to particulate dispersions, the selected bioactive agent(s) may be associated with, or incorporated in, the particles or perforated microstructures in any form that provides the desired efficacy and is compatible with the chosen production techniques. Similarly, the incorporated bioactive agent may be associated with the discontinuous phase of a reverse emulsion. As used herein, the terms "associate" or "associating" mean that the structural matrix, perforated microstructure, relatively non-porous particleor discontinuous phase may comprise, incorporate, adsorb, absorb, be coated with, or be formed by the bioactive agent. Where appropriate, the medicaments may be used in the form of salts (e.g. alkali metal or amine salts or as acid addition salts), or as esters, or as solvates (hydrates). In this regard, the form of the bioactive agents may be selected to optimize the activity and/or stability of the medicament and/or, to minimize the solubility of the medicament in the suspension medium.

It will further be appreciated that formulations according to the invention may, if desired, contain a combination of two or more active ingredients. The agents may be provided in combination in a single species of perforated microstructure or individually in separate species that are combined in the suspension medium or continuous phase. For example, two or more bioactive agents may be incorporated in a single feed stock preparation and spray dried to provide a single microstructure species comprising a plurality of medicaments. Conversely, the individual medicaments could be added to separate stocks and spray dried separately to provide a plurality of microstructure species with different compositions. These individual species could be added to, the medium in any desired proportion and placed in delivery systems as described below. Further, as briefly alluded to above, the perforated microstructures (with or without an associated medicament) may be combined with one or more conventionally micronized bioactive agents to provide the desired dispersion stability.

Based on the foregoing, it will be appreciated by those skilled in the art that a wide variety of bioactive agents may be incorporated in the disclosed stabilized dispersions. Accordingly, the list of preferred bioactive agents above is exemplary only and not intended to be limiting. It will also be appreciated by those skilled in the art that, the proper amount of bioactive agent and the timing of the dosages may be determined for the formulations in accordance with already-existing information and without undue experimentation.

As seen from the passages above, various components may be associated with, or incorporated in the perforated microstructures of tie present invention. Similarly, several techniques may be used to provide particulates having the desired morphology (e.g. a perforated or hollow/porous configuration) and density. Among other methods, perforated microstructures compatible with the instant invention may be formed by techniques including lyophilization, spray drying, multiple emulsion, micronization, or crystallization. It will further be appreciated that the basic concepts of many of these techniques area well known in the prior art and would not, in view of the teachings herein, require undue experimentation to adapt them so as to provide the desired perforated microstuctures.

While several procedures are generally compatible with the present invention, particularly preferred embodiments typically comprise perforated microstructures formed by spray drying. As is well known, spray drying is a one-step process that converts a liquid feed to a dried particulate form.

With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Büchi Ltd. or Nird Corp. will effectively produce particles of desired size. It will further be appreciated that these spray dryers, and specifically their atomizers, may be modified or customized for specialized applications, e.g. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

While typical spray-dried particles are approximately spherical in shape, nearly uniform in size and frequently hollow, there may be some degree of irregularity in shape depending upon the incorporated medicament and the spray drying conditions. In many instances the dispersion stability of spray-dried microspheres appears to be more effective if an inflating agent (or blowing agent) is used in their production. Particularly preferred embodiments may comprise, an emulsion with the inflating agent as the disperse or continuous phase (the other phase being aqueous in nature). The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such dispersions using this and other techniques are common and well known to those in the art. The blowing agent is preferably a fluorinated compound (e.g. perfluorohexane, perfluorooctyl bromide, perfluorodecalin, perfluorobutyl ethane) which vaporizes during the spray-drying process, leaving behind generally hollow, porous, aerodynamically light microspheres. As will be discussed in more detail below, other suitable blowing agents include chloroform, Freons and hydrocarbons. Nitrogen gas and carbon dioxide are also contemplated as a suitable blowing agent.

Although the perforated microstructures are preferably formed using a blowing agent as described above, it will be appreciated that, in some instances, no blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties such as, high in crystaminity, elevated melting temperature, surface activity, etc., that make it particularly suitable for use in such techniques.

When a blowing agent is employed, the degree of porosity of the perforated microstructure appears to depend, at least in part, on the nature of the blowing agent, its concentration in the feed stock (i.e. as an emulsion), and the spray drying conditions. With respect to controlling porosity it has surprisingly been found that the use of compounds, heretofore unappreciated as blowing agents, may provide perforated microstructures having particularly desirable characteristics. More particularly, in this novel and unexpected aspect of the present invention it has been found that the use of fluorinated compounds having relatively high boiling points (i.e. greater than about 60° C.) may be used to produce particulates that are especially suitable for inhalation therapies. In this regard it is possible to use fluorinated blowing agents having boiling points of greater than about 70° C., 80° C., 90° C. or even 95° C. Particularly preferred blowing agents have boiling points greater than the boiling point of water, i.e. greater than 100° C. (e.g. perflubron, perfluorodecalin). In addition, blowing agents with relatively low water solubility ($<10^{-6}$ M) are preferred since they enable the production of stable emulsion dispersions with mean weighted particle diameters less than 0.3 μm. As indicated above, these blowing agents will preferably be incorporated in an emulsified feed stock prior to spray drying. For the purposes of the present invention this feed stock will also preferably comprise one or more bioactive agents, one or more surfactants, or one or more excipients. Of course, combinations of the aforementioned components are also within the scope of the invention.

While not limiting the invention in any way it is hypothesized that, as the aqueous feed component evaporates during spray drying it leaves a thin crust at the surface of the particle. The resulting particle wall or crust formed during the initial moments of spray drying appears to trap any high boiling blowing agents as hundreds of emulsion droplets (ca. 200-300 nm). As the drying process continues, the pressure inside the particulate increases thereby vaporizing at least part of the incorporated blowing agent and forcing it through the relatively thin crust. This venting or outgassing apparently leads to the formation of pores or other defects in the crust. At the same time, remaining particulate components (possibly including some blowing agent) migrate from the interior to the surface as the particle solidifies. This migration apparently slows during the drying process as a result of increased resistance to mass transfer caused by an increased internal viscosity. Once the migration ceases the particle solidifies, leaving vesicles, vacuoles or voids where the emulsifying agent resided. The number of pores, their size, and the resulting wall thickness is largely dependent on the nature of the selected blowing agent (i.e. boiling point), its concentration in the emulsion, total solids concentration, and the spray-drying conditions.

It has been surprisingly found that substantial amounts of these relatively high boiling blowing agents may be retained in the resulting spray dried product. That is, the spray dried perforated microstructures may comprise as much as 5%, 10%, 20%, 30% or even 40% w/w of the blowing agent. In such cases, higher production yields were obtained as a result an increased particle density caused by residual blowing agent. It will be appreciated by those skilled in the art that this retained fluorinated blowing agent may alter the surface characteristics of the perforated microstructures and further increase the stability of the respiratory dispersions. Conversely, the residual blowing agent can generally be removed relatively easily with a post-production evaporation step in a vacuum oven. Optionally, pores may be formed by spray drying a bioactive agent and an excipient that can be removed from the formed microspheres under a vacuum.

In any event, typical concentrations of blowing agent in the feed stock are between 5% and 100% w/v, and more preferably between about 20% to 90% w/v. In other embodiments blowing agent concentrations will preferably be greater than about 10%, 20%, 30%, 40% 50% or even 60% w/v. Yet other feed stock emulsions may comprise 70%, 80%, 90% or even 95% w/v of the selected high boiling point compound.

In preferred embodiments, another method of identifying the concentration of blowing agent used in the feed is to provide it as a ratio of the concentration of the blowing agent to that of the stabilizing surfactant (i.e. phospholipid) in the precursor emulsion. For fluorocarbon blowing agents such as perfluorooctyl bromide and phosphatidylcholine, the ratio may be termed a perfluorocarboni/phosphatidylcholine ratio (or PFC/PC ratio). While phosphotidylcholine is a preferred surfactant, those skilled in the art will appreciate that other surfactants may provide acceptable emulsions and may be substituted therefore. In any event, the PFC/PC ratio will typically range from about 1 to about 60 and more preferably from about 10 to about 50. For preferred embodiments the ratio will, generally be greater than about 5, 10, 20, 25, 30, 40 or even 50. In this respect, it will be appreciated that higher PFC/PC ratios typically lead to particulates exhibiting greater porosity. Accordingly, altering the PFC/PC ratio in the feed stock emulsion may advantageously control the morphology of the resulting microstructures. In this regard, the use of higher PFC/PC ratios tends to provide structures of a more hollow and porous nature. More particularly, those methods employing a PFC/PC ratio of greater than about 4.8 tended to provide structures that are particularly compatible with the dispersions disclosed herein.

While relatively high boiling point blowing agents comprise one preferred aspect of the instant invention, it will be appreciated that more conventional blowing or inflating agents may also be used to provide compatible perforated microstructures. Generally, the inflating agent can be any material that will turn to a gas at some point during the spray drying or post-production process. Suitable agents include:

1. Dissolved low-boiling (below 100° C.) solvents with limited miscibility with aqueous solutions, such as methylene chloride, acetone and carbon disulfide used to saturate the solution at room temperature.
2. A gas, e.g. CO2 or N2, used to saturate the solution at room temperature and levated pressure (e.g. 3 bar). The droplets are then supersaturated with the gas at atmosphere and 100° C.
3. Emulsions of immiscible low-boiling (below 100° C.) liquids such as Freon 113, perfluoropentane, perfluorohexane, perfluorobutane, pentane, butane, FC-11, FC-11B1, FC-11B2, FC-12B2, FC-21, FC-21B1, FC-21B2, FC-31B1, FC113A, FC-122, FC-123, FC-132, FC-133, FC-141, FC-141B, FC-142, FC-151, FC-152, FC-1112, FC-1121 and FC-1131.

With respect to these lower boiling point inflating agents, they are typically added to the feed stock in quantities of about 1% to 80% w/v of the surfactant solution. Approximately 30% w/v inflating agent has been found to produce a spray dried powder that may be used to form the stabilized dispersions of the present invention.

Regardless of which blowing agent is ultimately selected, it has been found that compatible perforated microstructures may be produced particularly efficiently using a Büchi mini spray drier (model B-191; Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably these temperatures will be from 90° C. to 120° C. for the inlet and from 60° C. to 90° C. for the outlet. The flow rate that is used in the spray drying equipment will generally be about 3 ml per minute to about 15 ml per minute. The atomizer air flow rate may vary between values of 1,200 liters per hour, to about 3,900 liters per hour. Commercially available spray dryers are well known to those in the art, and suitable settings for any particular dispersion can be readily determined through standard empirical testing; with due reference to the examples that follow. Of course, the conditions may be adjusted so as to preserve biological activity in larger molecules such as proteins or peptides.

Particularly preferred embodiments of the present invention comprise spray drying preparations comprising a surfactant such as a phospholipid and at least one bioactive agent. In other embodiments the spray drying preparation may further comprise an excipient comprising a hydrophilic moiety such as, for example, a carbohydrate (i.e. glucose, lactose, or starch) in addition to any selected surfactant. In this regard various starches and derivatized starches suitable for use in the present invention. Other optional components may include conventional viscosity modifiers buffers such as phosphate buffers or other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

Whatever components are selected, the first step in particulate production typically comprises feed stock preparation. Preferably the selected drug is dissolved in water to produce a concentrated solution. The drug may also be dispersed directly in the emulsion, particularly in the case of water insoluble agents. It will also be appreciated that the drug may be incorporated in the form of a solid particulate dispersion. The concentration of the a drug used is dependent on the dose of drug required in the final powder and the performance of the MDI drug suspension (e.g., fine particle dose). As needed, cosurfactants such as poloxamer 188 or span 80 may be added to this annex solution. Additionally, excipients such as sugars and starches can also be added.

In selected embodiments an oil-in-water emulsion is then formed in a separate vessel. The oil employed is preferably a fluorocarbon (e.g., perfluorooctyl bromide, perfluorodecalin) which is emulsified using a surfactant such as a long chain saturated phospholipid. For example, one gram of phospholipid may be homogenized in 150 g hot distilled water (e.g., 60° C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting perfluorocarbon in water emulsion is then processed using a high pressure homogenizer to reduce the particle size. Typically the emulsion is processed at 12,000 to 18,000 psi for 5 discrete passes and kept at 50 to 80° C.

The drug solution and perfluorocarbon emulsion are then combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the bioactive agent may be solubilized (or dispersed) directly in the emulsion. In such cases, the bioactive emulsion is simply spray dried without combining separate drug preparation.

In any event, operating conditions such as inlet and outlet temperature, feed rate, atomization pressure, flow rate of the drying air, and nozzle configuration can be adjusted in accordance with the manufacturer's guidelines in order to produce the required particle size; and production yield of the resulting dry microstructures. Exemplary settings are as follows: an air inlet temperature between 60° C. and 170° C.; an air outlet between 40° C. to 120° C.; a feed rate between 3 ml to about 15 ml per minute; and an aspiration setting of 100% and an atomization air flow rate between 1,200 to 2,800 L/hr. The selection of appropriate apparatus and processing conditions are well within the purview of a skilled artisan in view of the teachings herein and may be accomplished without undue experimentation. In any event, the use of these and substantially equivalent methods provide for the formation of hollow porous aerodynamically light microspheres with particle diameters appropriate for aerosol deposition into the lung.

Along with spray drying the perforated microstructures of the present invention may be formed by lyophilization. Those skilled in the art will appreciate that lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in the perforated microstructures without compromising physiological activity. Methods for providing lyophilized particulates are known to those of skill in the art and it would clearly not require undue experimentation to provide dispersion compatible microstructures in accordance with the teachings herein. Accordingly, to the extent that lyophilization processes may be used to provide microstructures having the desired porosity and size they are conformance with the teachings herein and are expressly contemplated as being within the scope of the instant invention.

Besides the aforementioned techniques, the perforated microstructures of the present invention may also be formed using a double emulsion method. In the double emulsion method the medicament is first dispersed in a polymer dissolved in an organic solvent (e.g. methylene chloride) by sonication or homogenization. This primary emulsions then stabilized by forming a multiple emulsion in a continuous aqueous phase containing an emulsifier such as polyvinylalcohol. Evaporation or extraction using conventional techniques and apparatus then removes the organic solvent. The resulting microspheres are washed, filtered and dried prior to combining them with an appropriate suspension medium in accordance with the present invention.

Regardless of how the microstructures or particles are formed, the selected suspension media used to provide the desired stabilized dispersion is preferably compatible with pulmonary administration. In general, the selected suspension medium should be biocompatible (i.e. relatively non-toxic) and non-reactive with respect to the suspended perforated microstructures comprising the bioactive agent. Preferred embodiments comprise suspension media selected from the group consisting of fluorochemicals, fluorocarbons (including those substituted with other halogens), perfluorocarbons, fluorocarbon/hydrocarbon diblocks, hydrocarbons, alcohols, ethers, or combinations thereof. It will be appreciated that the suspension medium may comprise a mixture of various compounds selected to impart specific characteristics. It will also be appreciated that the perforated microstructures are preferably insoluble in the suspension medium, thereby providing for stabilized medicament particles, and effectively protecting a selected bioactive agent from degradation, as might occur during prolonged storage in an aqueous solution. In preferred embodiments, the selected suspension medium is bacteriostatic.

As indicated above, the suspension media may comprise any one of a number of different compounds including hydrocarbons, fluorocarbons or hydrocarbon/fluorocarbon diblocks. In general, the contemplated hydrocarbons or highly fluorinated or perfluorinated compounds may be linear, branched or cyclic, saturated or unsaturated compounds. Conventional structural derivatives of these fluorochemicals and hydrocarbons are also contemplated as being within the scope of the present invention. Selected embodiments comprising these totally or partially fluorinated compounds may contain one or more hetero-atoms including bromine or chlorine. Preferably, these fluorochemicals comprise from 1 to 16 carbon atoms and include, but are not limited to, linear, cyclic or polycyclic perfluoroaacanes, bis(perfluoroalkyl)alkenes, perfluoroethers, perfluoroamines, perfluoroalkyl bromides and perfluoroalkyl chlorides such as dichlorooctane. Particularly preferred fluorinated compounds for use in the suspension medium may comprise perfluorooctyl bromide, $C_8F_{17}Br$ (PFOB or perflubron), dichlorofluorooctane $C_8F_{16}Cl_2$, and the hydrofluoroalkane perfluorooctyl ethane $C_8F_{17}C_2H_5$ (PFOE). In selected embodiments the suspension medium will comprise a compound (particularly a fluorochemical) having a positive spreading coefficient. Other useful preparations may comprise perfluorohexane or perfluoropentane as suspension media.

More generally, exemplary fluorochemicals which are contemplated for use in the present invention generally include halogenated fluorochemicals (i.e. $C_nF_{2n+1}X$, $XC_nF_{2n}X$, where n=2–10, X=Br, Cl or I) and, in particular, 1-bromo-F-butane n-$C_4F_9Br$, 1-bromo-F-hexane (n-$C_6F_{13}Br$), 1-bromo-F-heptane (n-$C_7F_{15}Br$) 1,4-dibromo-F-butane and 1,6-dibromo-F-hexane. Other useful brominated fluorochemicals are disclosed in U.S. Pat. No. 3,975,512 to Long, which is incorporated herein by reference. Specific fluorochemicals having chloride substituetnts, such as perfluorooctyl chloride (n-$C_8F_{17}Cl$), 1,8-dichloro-F-heptane (n-$ClC_8F_{16}Cl$), 1,6-dichloro-F-hexane (n-$ClC_6F_{12}Cl$), and 1,4-dichloro-F-butane (n-$ClC_4F_8Cl$) are also preferred.

Fluorocarbons, fluorocarbon-hydrocarbon compounds and halogenated fluorochemicals containing other linkage groups, such as esters, thioethers and amines are also suitable for use as suspension media in the present invention. For instance, compounds having the general formula, $C_{n2n+1}OC_mF_{2n+1}$, or $C_nF_{2n+1}CH{=}CHC_mF_{2m+1}$, (as for example $C_4F_9CH{=}CHC_4F_9$ (F-44E), i-$C_3F_9CH{=}CHC_6F_{13}$ (F-i36E), and $C_6F_{13}CH{=}CHC_6F_{13}$ (F-66E)) where n and m are the same or different and n and m are integers from about 2 to about 12 are compatible with teachings herein. Useful fluorochemical-hydrocarbon diblock and triblock compounds include those with the general formulas $C_nF_{2n+1}—C_mH_{2m+1}$ and $C_nF_{2n+1}C_mH_{2m-1}$, where n=2-12; m=2-16 or $C_pH_{2p+1}—C_nF_{2m}—C_mH_{2m+1}$, where p=1-12, m=1-12 and n=2-12. Preferred compounds of this type include $C_8F_{17}C_2H_5$, $C_6F_{13}C_{10}H_{21}$, $C_8F_{17}C_8H_{17}$, $C_6F_{13}CH{=}CHC_6H_{13}$ and $C8F_{17}CH{=}CHC_{10}H_{21}$. Substituted ethers or polyethers (i.e. $XC_nF_{2n}OC_mF_{2m}X$, $XCFOC_nF_{2n}OCF_2X$, where n and m=1-4, X=Br, Cl or l) and fluorochemical-hydrocarbon ether diblocks or triblocks (i.e. $C_nF_{2+1}O—C_mH_{2m+1}$, where n=2-10; m=2-16 or $C_pH_{2p+1}—O—C_nF_{2n}—O—C_mH_{2m+1}$, where p=2-12, m=1-12 and n=2-12) may also used as well as $C_nF_{2n+1}O—C_mF_{2m}OC_pH_{2p+1}$, wherein n, m and p are from 1-12. Furthermore, depending on the application, perfluoroalkylated ethers or polyethers may be compatible with the claimed dispersions.

Polycyclic and cyclic fluorochemicals, such as $C_{10}F_{18}$ (F-decalin or perfluorodecalin), perfluoroperhydrophenanthrene, perfluorotetramethylcyclohexane (AP-144) and perfluoro n-butyldecalin are also within the scope of the invention. Additional useful fluorochemicals include perfluorinated amines, such as F-tripropylamine ("FTPA") and F-tributylamine ("FTBA"). F-4-methyloctahydroquinolizine ("FMOQ"), F-N-methyl-decahydroisoquinoline ("FMIQ"), F-N-methyldecaliydroquinoline ("FHQ"), F-N-cyclohexylpyrrolidine ("FCHP") and F-2-butyltetrahydrofuran ("FC-75" or "FC-77"). Still other useful fluorinated compounds include perfluorophenanthrene, perfluoromethyldecalin, peifuorodimethyletliylcyclohexane, perfluorodimethyldecal in, perfluorodiethyldecal in, perfluorornethyladamantane, perfluorodimethyladamantane. Other contemplated fluorochemicals having nonfluorine substituents, such as, perfluorooctyl hydride, arid similar compounds having different numbers of carbon atoms are also useful. Those skilled in the art will further appreciate that other variously modified fluorochemicals are encompassed within the broad definition of fluorochemical as used in the instant application and suitable for use in the present invention. As such, each of the foregoing compounds may be used, alone or in combination with other compounds to form the stabilized dispersions of the present invention.

Yet other specific fluorocarbons, or classes of fluorinated compounds, that may be useful as suspension media include, but are not limited to, fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluoiobutane, fluorocyclobutane, fluoropropane, fluoroethers, fluoropolyethers and fluorotriethylamines. Such compounds are generally environmentally sound and are biologically non-reactive.

While any biocompatible fluid compound may be used in conjunction with the present invention, the selected suspension medium will preferably have a vapor pressure less than about 5 atmospheres and more preferably less than about 2 atmospheres. Unless otherwise specified, all vapor pressures recited herein are measured at 25° C. In other embodiments, preferred suspension media compounds will have vapor pressures on the order of about 5 torr to about 760 torr, with more preferable compounds having vapor pressures on the order of from about 8 torr to about 600 torr, while still more preferable compounds will have vapor pressures on the order of from about 10 torr to about 350 torr. Such suspension media may be used in conjunction with compressed air nebulizers, ultrasonic nebulizers or with mechanical atomizers to provide effective ventilation therapy. Moreover, more volatile compounds may be mixed with lower vapor pressure components to provide suspension media having specified physical characteristics selected to further improve stability or enhance the bioavailability of the dispersed bioactive agent.

Other embodiments of the present invention will comprise suspension media that boil at selected temperatures under ambient conditions (i.e. 1 atmosphere). For example, preferred embodiments will comprise suspension media compounds that boil above 0° C., above 5° C., above 10° C., above 15° C., or above 20° C. In other embodiments, the suspension media compound may boil at or above 25° C. or at or above 30° C. In yet other embodiments; the selected suspension media compound may boil at or above human body temperature (i.e. 37° C.), above 45° C., 55° C., 65° C., 75° C., 85° C. or above 100° C.

The stabilized suspensions or dispersions of the present invention may be prepared by dispersal of the microstructures in the selected suspension medium, which may then be placed in a container or reservoir. In this regard, the stabilized preparations of the present invention can be made by simply combining the components in sufficient quantity to produce the final desired dispersion concentration. Although the microstructures readily disperse without mechanical energy, the application of mechanical energy to aid in dispersion (e.g. with the aid of sonication) is contemplated, particularly for the formation of stable emulsions or reverse emulsions. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

It will also be understood that other components can be included in the pharmaceutical compositions of the present invention. For example, osmotic agents, stabilizers, chelators, buffers, viscosity modulators, salts, and sugars can be added to fine tune the stabilized dispersions for maximum life and ease of administration. Such components may be added directly to the suspension medium, ether phase of an emulsion or associated with, or incorporated in, dispersed particles or perforated microstructures. Considerations such as sterility, isotonicity, and biocompatibility may govern the use of conventional additives to the disclosed compositions. The use of such agents will be understood to those of ordinary skill in the art and, the specific quantities, ratios, and types of agents can be determined empirically without undue experimentation.

The stabilized dispersions of the invention may also comprise one or more additives to further enhance stability or increase biocompatibility. For example, various surfactants, co-solvents, osmotic agents, stabilizers, chelators, buffers, viscosity modulators, solubility modifiers and salts can be associated with the perforated microstructure, suspension medium, or both. The use of such additives will be understood to those of ordinary skill in the art and, the specific quantities, ratios, and types of agents can be determined empirically without undue experimentation.

The stabilized suspensions or dispersions of the present invention may be prepared by dispersal of the microstructures in the selected suspension medium that may then be placed in a container or reservoir. In this regard, the stabilized preparations of the present invention can be made by simply combining the components in sufficient quantity to produce the final desired dispersion concentration. That is, the components of the preparations may be combined to provide a respiratory blend. Although the microstructures readily disperse without mechanical energy, the application of mechanical energy (e.g. sonication) to the respiratory blend to mix the components or aid in their dispersion is contemplated. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

It will be appreciated that conventional pharmaceutical equipment and methodology may be used during production of the disclosed dispersions. For example, commercially available spray drying and mixing equipment may be used to form the perforated microstructures and desired suspensions. Accordingly, it is submitted that the skilled artisan would have little trouble producing the pharmaceutical dispersions of the present invention on a commercial scale when in possession of the instant disclosure.

It will further be appreciated that the stabilized preparations of the present invention may be advantageously supplied to the physician or other health care professional, in a sterile, prepackaged or kit form. More particularly, the formulations may be supplied as stable, preformed dispersions ready for administration or, as separate ready to mix components. When provided in a ready to use form, the dispersions may be packaged in single use containers or reservoirs (e.g. in glass vials comprising a few milliliters of the dispersion) or in multi-use containers or reservoirs. When provided as individual components (e.g., as powdered microspheres and as neat suspension medium) the stabilized preparations may then be formed at any time prior to use by simply combining the contents of the containers as directed. For example, a small volume of concentrated dispersion could be diluted in a larger volume of neat fluorocarbon prior to its use in liquid ventilation. Additionally, due to the superior stability of the disclosed preparations, the kits may contain a number of ready to mix, or prepackaged dispersions in a single use form so that the user can readily select or modify the therapeutic regimen for the particular indication. In this regard, each of the containers may be fitted with a septum for direct removal of the dispersion or with appropriate tubing, cannulas, Luer fittings, etc. for association with a ventilator or endotracheal apparatus. It will also be appreciated that such kits may optionally include a bronchoscope or endotracheal apparatus (or components thereof) for administration of the preparations.

Administration of bioactive agent may be indicated for the treatment of mild, moderate or severe, acute or chronic symptoms or for prophylactic treatment. Moreover, the bioactive agent may be administered to treat local or systemic conditions or disorders. In this regard, one particularly preferred embodiment comprises the systemic administration (e.g. delivery to the systemic circulation of a patient via the pulmonary air passages) of a bioactive agent. It will further be appreciated that the precise dose administered will depend on the age and condition of the patient, the particular medicament used and the frequency of administration and will ultimately be at the discretion of the attendant physician. When dispersions comprising combinations of bioactive agents are administered, the dose of each agent will generally be that employed for each agent when used alone.

Direct administration of bioactive compounds is particularly effective in the treatment of pulmonary disorders especially where poor vascular circulation of diseased portions of a lung reduces the effectiveness of intravenous drug delivery. Accordingly, stabilized dispersions administered to the lung may prove useful in the treatment and/or diagnosis of disorders such as respiratory distress syndrome, acute respiratory distress syndrome, lung contusions, divers lung, post traumatic respiratory distress, post surgical atelectasis, septic shock, multiple organ failure, Mendelssohn's disease, obstructive lung disease, pneumonia, pulmonary edema, impaired pulmonary circulation, cystic fibrosis and lung cancer. In this regard, the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

As discussed throughout the instant specification, the compositions of the present invention may be administered to the lung using a pulmonary delivery conduit. Those skilled in the art will appreciate the term "pulmonary delivery conduit", as used herein, shall be construed in a broad sense to comprise any device or apparatus, or component thereof, that provides for the instillation or administration of a liquid in the lungs. In this respect a pulmonary delivery conduit or delivery conduit shall be held to mean any bore, lumen, catheter, tube, conduit, syringe, actuator, mouthpiece, endotracheal tube or bronchoscope that provides for the administration or instillation of the disclosed dispersions to at least a portion of the pulmonary air passages of a patient in need thereof. It will be appreciated that the delivery conduit may or may not be associated with a liquid ventilator or gas ventilator. In particularly preferred embodiments the delivery conduit shall comprise an endotracheal tube or bronchoscope.

Accordingly, liquid dose instillation preferably involves the instillation of the perforated microstructures in a suitable suspension medium to an intubated patient through an endotracheal tube, or to a free-breathing patient via bronchoscope. Other embodiments comprise the administration of the disclosed dispersions directly into the throat. That is, the formulations of the present invention may be "trickled" into the lungs of the patient as a bolus using standard tubing and/or a syringe: Here it must be emphasized that the dispersions of the present invention may be administered to ventilated (e.g. those connected to a mechanical ventilator) or nonventilated, patients (e.g. those undergoing spontaneous respiration). Accordingly, in preferred embodiments the methods and systems of the present invention may comprise the use or inclusion of a mechanical ventilator. Further, the stabilized dispersions of the present invention may also be used as a lavage agent to remove debris in the lung, or for diagnostic lavage procedures. In any case the introduction of liquids, particularly fluorochemicals, into the lungs of a patient is well known and could be accomplished by a skilled artisan in possession of the instant specification without undue experimentation.

It will be understood that, in connection with the present invention, the disclosed dispersions are preferably administered directly to at least a portion of the pulmonary air passages of a mammal. As used herein, the terms "direct instillation" or "direct administration" shall be held to mean the introduction of a stabilized dispersion into the lung cavity of a mammal. That is, the dispersion will preferably be administered through the trachea of a patient and into the lungs as a liquid. While the dispersions may be administered in the form of an aerosol or nebulized liquid, they will preferably be introduced as a volume of a relatively free flowing liquid passing through a delivery conduit and into the pulmonary air passages. In this regard, the flow of the dispersion may be gravity assisted or may be afforded by induced pressure such as through a pump or the compression of a syringe plunger. In any case, the amount of dispersion administered may be monitored by mechanical devices such as flow meters or by visual inspection.

It will further be appreciated that, liquid ventilation (partial or total) involves the introduction of a respiratory promoter (typically a fluorochemical) to the lung for the promotion of physiological gas exchange. For partial liquid ventilation, the patient is preferably ventilated using a mechanical ventilator following pulmonary introduction of the liquid. In accordance with the teachings herein the respiratory promoter may comprise a stabilized dispersion. For example, perforated microparticles comprising penicillin may be suspended in perfluorooctyl bromide to provide a stabilized dispersion that could be used for liquid ventilation. This dispersion could then be administered, at any volume up to functional residual capacity (FRC), to the lung of a patient as described in U.S. Pat. Nos. 5,562,608, 5,437,272, 5,490,498, 5,667,809, 5,770,585 and 5,540,225 each of which is incorporated herein by reference.

Alternatively, a concentrated, but relatively stable, dispersion could be packaged in a single dose configuration having a total volume on the order of a few milliliters or less. It will be appreciated that the relatively small volume could be administered directly to the lung. However, in preferred embodiments this concentrated dispersion could be mixed with a larger volume of neat respiratory promoter (which may be the same or different as the suspension medium) prior to introduction to the lung. In still other embodiments the concentrated dispersion could be administered directly to the lung of a patient already containing respiratory promoter. That is, for intubated patients undergoing partial liquid ventilation, the bioactive agent suspension may be top-loaded onto an existing volume of a fluorochemical. In each of these cases, the respiratory promoter and/or suspension medium will provide for the efficient dispersal and deposition of the bioactive perforated microspheres on the lung membrane.

More specifically, by providing for the administration of bioactive agents in what can be a relatively anhydrous environment, i.e. in a fluorochemical, physiological uptake of the agent may be dramatically increased. This is particularly true of lung surfactants such as phospholipids. As discussed more fully in Example XIV below the adsorption time for surfactant is exponentially decreased when it is brought into contact with a wetted surface (lung membrane) by a fluorochemical as opposed to an aqueous solution. This is because adsorption of the surfactant from an anhydrous suspension medium into an aqueous environment is thermodynamically very favorable. By way of contrast, there is no large driving force when the surfactant is moving from one aqueous medium to another. Accordingly, particularly preferred embodiments of the present invention comprise perforated microstructures associated with, or incorporating, natural or synthetic surfactants distributed in a fluorocheinical suspension medium.

While the stabilized dispersions may be administered up to the functional residual capacity of the lungs of a patient, it will be appreciated that selected embodiments will comprise the pulmonary administration of much smaller volumes (e.g. on the order of a milliliter or less). For example, depending on the disorder to be treated, the volume administered may be on the order of 1, 3, 5, 10, 20, 50, 100, 200 or 500 milliliters. In preferred embodiments the liquid volume is less than 0.25 or 0.5 percent FRC. For particularly preferred embodiments, the liquid volume is 0.1 percent FRC or less. With respect to the administration of relatively low volumes of stabilized dispersions it will be appreciated that the wettability and spreading characteristics of the suspension media (particularly fluorochemicals) will facilitate the even distribution of the bioactive agent in the lung. However, in other embodiments it may be preferable to administer the suspensions a volumes of greater than 0.5, 0.75 or 0.9 percent FRC. In any event, LDI treatment as disclosed herein represents a new alternative for critically ill patients on mechanical ventilators, and opens the door for treatment of less ill patients with bronchoscopic administration.

While the stabilized dispersions of the present invention are particularly suitable for the pulmonary administration of bioactive agents, they may also be used for the localized or systemic administration of compounds to any location of the body. Accordingly, it should be emphasized that, in preferred embodiments, the formulations may be administered using a number of different routes including, but not limited to, the gastrointestinal tract, the respiratory tract, topically, intramuscularly, intraperitoneally, nasally, vaginally, rectally, aurally, orally or ocular. More generally, the stabilized dispersions of the present invention may be used to deliver agents topically or by administration to a non-pulmonary body cavity. In preferred embodiments the body cavity is selected from the group consisting of the peritoneum, sinus cavity, rectum, urethra, gastrointestinal tract, nasal cavity, vagina, auditory meatus, oral cavity, buccal pouch and pleura. Among other indications, stabilized dispersions comprising the appropriate bioactive agent, (e.g. an antibiotic or an anti-inflammatory), may be used to treat infections of the eye, sinusitis, infections of the auditory tract and even infections or disorders of the gastrointestinal tract. With respect to the latter, the dispersions of the present invention may be used to selectively deliver pharmaceutical compounds to the lining of the stomach for the treatment of *H. pylori* infections or other ulcer related disorders.

The foregoing description will be more fully understood with reference to the following Examples. Such Examples, are, however, merely representative of preferred methods of practicing the present invention and should not be read as limiting the scope of the invention.

EXAMPLE I

Preparation of Hollow Porous Particles of Gentamicin Sulfate by Spray-Drying 40 to 60 ml of the following solutions were prepared for spray drying: 50% w/w hydrogenated phosphatidylcholine, E-100-3 (Lipoid KG, Ludwigshafen, Germany) 50% w/w gentamicin sulfate (Amresco, Solon, Ohio) Perfluorooctylbromide, Perflubron (NMK, Japan) Deionized water Perforated microstructures comprising gentamicin sulfate were prepared by a spray drying technique using a B-191 Mini Spray-Drier (Büchi, Flawil, Switzerland) under the following conditions: aspiration: 100%, inlet temperature: 85° C.; outlet temperature: 61° C.; feed pump: 10%; $N_2$ flow: 2,800 L/hr. Variations in powder porosity were examined as a function of the blowing agent concentration.

Fluorocarbon-in-water emulsions of perfluorooctyl bromide containing a 1:1 w/w ratio of phosphatidylcholine (PC), and gentamicin sulfate were prepared varying only the PFC/PC ratio. 1.3 grains of hydrogenated egg phosphatidylcholine was dispersed in 25 mL deionized water using an Ultra-Turrax mixer (model T-25) at 8000 rpm for 2 to 5 minutes (T=60-70° C.). A range from 0 to 40 grams of perflubron was added dropwise during mixing (T=60-70° C.). After addition was complete, the fluorocarbon-in-water emulsion was mixed for an additional period of not less than 4 minutes. The resulting coarse emulsions were then homogenized under high pressure with an Avestin (Ottawa, Canada) homogenizer at 15,000 psi for 5 passes. Gentamicin sulfate was dissolved in approximately 4 to 5 mL deionized water and subsequently mixed with the perflubron emulsion immediately prior to the spray dry process. The gentamicin powders were then obtained by spray drying using the conditions described above. A free flowing pale yellow powder was obtained for all perflubron containing formulations. The yield for each of the various formulations ranged from 35% to 60%.

EXAMPLE II

Morphology of Gentamicin Sulfate Spray-Dried Powders

A strong dependence of the powder morphology, degree of porosity, and production yield was observed as a function of the PFC/PC ratio by scanning electron microscopy (SEM), of the samples obtained in Example I. In the micrographs, the porosity and surface roughness was found to be highly dependent on the concentration of the blowing agent, where the surface roughness, number and size of the pores increased with increasing PFC/PC ratios. For example, the formulation devoid of perfluorooctyl bromide produced microstructures that appeared to be highly agglomerated and readily adhered to the surface of the glass vial. Similarly, smooth, spherically shaped microparticles were obtained when relatively little (PFC/PC ratio=1.1 or 2.2) blowing agent was used. However, as the PFC/PC ratio increased, the particles showed dramatic increases in porosity and surface roughness.

As revealed by transmission electron microscopy (TEM) cross sections of the particles revealed that the hollow nature of the microstructures was also enhanced by the incorporation of additional blowing agent. In this regard, both the hollow nature and wall thickness of the resulting perforated microstructures appeared to be largely dependent on the concentration of the selected blowing agent. That is, the hollow nature of the preparation appeared to increase and the thickness of the particle walls appeared to decrease as the PFC/PC ratio increased. Substantially non-porous, relatively solid structures were obtained from formulations containing little or no fluorocarbon blowing agent. Conversely, the perforated microstructures produced using a relatively high PFC/PC ratio of approximately 45 proved to be extremely hollow with a relatively thin wall ranging from about 43.5 to 261 nm. In keeping with the teachings herein, both types of particles are compatible for use in the present invention.

EXAMPLE III

Preparation of Hollow Porous Particles of Albuterol Sulfate by Spray-Drying

Hollow porous albuterol sulfate particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve 1 g of albuterol sulfate (Accurate Chemical, Westbury, N.Y.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid KG, Ludwigshafen, Germany), was homogenized in 150 g of hot deionized water (T=50 to 60° C.) using an Ultra-Turrax mixer (model T-25) at 8000 rpm for 2 to 5 minutes (T 60-70° C.). 25 g of perfluorooctyl bromide (Atochern, Paris, France) was added dropwise during mixing. After the fluorocarbon was added, the emulsion was mixed for a period of not less than 4 minutes. The resulting coarse emulsion was then passed through a high pressure homogenizer (Avestin, Ottawa, Canada) at 18,000 psi for 5 passes.

Solutions A and B were combined and fed into the spray-dryer under the conditions described above. A free flowing white powder was collected at the cyclone separator. The hollow porous albuterol sulfate particles had a volume-weighted mean aerodynamic diameter of 1.18±1.42 μm as determined by a time-of-flight analytical method (Aerosizer, Amherst Process Instruments, Amherst, Mass.). Scanning electron microscopy (SEM) analysis showed the powders to be spherical and highly porous. The tap density of the powder was determined to be less than 0.1 g/cm$^3$.

This foregoing example serves to illustrate the inherent diversity of the present invention as a drug delivery platform capable of effectively incorporating any one of a number of pharmaceutical agents. The principle is further illustrated in the next example.

EXAMPLE IV

Formation of Porous Particulate Microstructures Comprising Mixture of Long-Chain/Short-Chain Phospholipids and Albuterol Sulfate A dispersion for spray-drying was prepared as described in Example III above, with the difference that 1 g of DSPC was dispersed with 100 mg of a short-chain phospholipid, dioctylphosphatidylcholine (DOPC) (Avanti Polar Lipids, Alabaster, Ala.). The composition of the spray feed is shown in Table II immediately below. The resulting yield was 50%.

TABLE II

Composition of the Spray Feed

| Component | Quantity |
|---|---|
| Disteroylphosphatidylcholine (DSPC) | 1 g |
| Dioctanoylphosphatidylcholine (DOPC) | 0.1 g |
| Albuterol Sulfate | 1 g |
| Perfluorohexane | 1 g |
| Water | 60 g |

EXAMPLE V

Preparation of Hollow Porous Particles of Cromolyn Sodium by Spray-Drying

Perforated microstructures comprising cromolyn sodium were prepared by a spray-drying technique with a B-191 Mini Spray-Drier (Büchi, Flawil, Switzerland) under the following spray conditions: aspiration: 100%, inlet temperature: 85° C.; outlet temperature: 610° C.; feed pump: 10%; $N_2$ flow: 2,800 L/hr. The feed solution was prepared by mixing two solutions A and B immediately prior to spray drying.

Solution A: 20 g of water was used to dissolve 1 g of cromolyn sodium (Sigma Chemical Co, St. Louis, Mo.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid KG, Ludwigshafen, Germany), was homogenized in 1 S0 g of hot deionized water (T=50 to 60° C.) using an Ultra-Turrax mixer (model T-25) at 8000 rpm for 2 to 5 minutes (T=60-70° C.). 27 g of perfluorodecalin (Air Products, Allentown, Pa.) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing pale yellow powder was collected at the cyclone separator. The hollow porous cromolyn sodium particles had a volume-weighted mean aerodynamic diameter of 1.23±1.31 μm as determined by a time-of-flight analytical method (Aerosizer, Amherst Process Instruments, Amherst, Mass.). Scanning electron microscopy (SEM) analysis showed the powders to be both hollow and porous. The tap density of the powder was determined to be less than 0.1 g/cm$^3$.

EXAMPLE VI

Preparation of Hollow Porous Particles of BDP by Spray-Drying

Perforated microstructures comprising beclomethasone dipropionate (BDP) particles were prepared by a spray-drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed stock was prepared by mixing 0.11 g of lactose with a fluorocarbon-in-water emulsion immediately prior to spray drying. The emulsion was prepared by the technique described below.

74 mg of BDP (Sigma, Chemical Co., St. Louis, Mo.), 0.5 g of EPC-100-3 (Lipoid KG, Ludwigshafen, Germany), 15 mg sodium oleate (Sigma); and 7 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60-70° C.). 8 g of perflubron (Atochem, Paris, France) was added dropwise during mixing. After the addition was complete, the emulsion was mixed for an additional period of not less than 4 minutes. The resulting coarse emulsion was then passed through a high pressure homogenizer (Avestin, Ottawa, Canada) at 18,000 psi for 5 passes. This emulsion was then used to form the feed stock that was spray dried as described above. A free flowing white powder was collected at the cyclone separator. The hollow porous BDP particles had a tap density of less than 0.1 g/cm$^3$.

EXAMPLE VII

Preparation of Hollow Porous Particles of TAA by Spray-Drying

Perforated microstructures comprising triamcinolone acetonide (TAA) particles were prepared by a spray drying technique with a B-191 Mini Spray-Drier (Büchi, Flawil, Switzerland) under the following spray conditions: aspiration: 100%, inlet temperature: 85° C.; outlet temperature: 61° C.; feed pump: 10%; $N_2$ flow: 2,800 L/hr. The feed stock was prepared by mixing 0.57 g of lactose with a fluorocarbon-in-water emulsion immediately prior to spray drying. The emulsion was prepared by the technique described below. 100 mg of TAA (Sigma, Chemical Co., St. Louis, Mo.), 0.56 g of EPC-100-3 (Lipoid KG, Ludwigshafen, Germany), 25 mg sodium oleate (Sigma), and 13 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60 to 70° C.). 8 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes. This emulsion was then used to form the feed stock that was spray dried as described above. A free flowing white powder was collected at the cyclone separator. The hollow porous TAA particles had a tap density of less than 0.1 g/cm$^3$.

EXAMPLE VIII

Preparation of Hollow Porous Particles of DNase I by Spray-Drying

Hollow porous DNase I particles were prepared by a spray drying technique with a B-191 Mini Spray-Drier (Büchi, Flawil, Switzerland) under the following conditions: aspiration: 100%, inlet temperature: 80° C.; outlet temperature: 61° C.; feed pump: 10%; $N_2$ flow: 2,800 L/hr. The feed was prepared by mixing two solutions A and B immediately prior to spray drying.

Solution A: 20 g of water was used to dissolve 0.5 gr of human pancreas DNase I (Calbiochem, San Diego Calif.) and 0.012 g of poloxamer 188 NF grade (BASF, Mount Olive, N.J.).

Solution B: A fluorocarbon-in-water emulsion stabilized by phospholipid was prepared in the following way. The phospholipid, 0.52 g EPC-100-3 (Lipoid KG, Ludwigshafen, Germany), was homogenized in 87 g of hot deionized water (T=50 to 60° C.) using an Ultra-Turrax mixer (model T-25) at 8000 rpm for 2 to 5 minutes (T=60-70° C.). 13 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing pale yellow powder was collected at the cyclone separator. The hollow porous DNase I particles had a volume-weighted mean aerodynamic diameter of 1.29±1.40 μm as determined by a time-of-flight analytical method (Aerosizer, Amherst Process Instruments, Amherst, Mass.). Scanning electron microscopy (SEM) analysis showed the powders to be both hollow and porous. The tap density of the powder was determined to be 3 less than 0.1 g/cm$^3$.

The foregoing example further illustrates the extraordinary compatibility of the present invention with a variety of bioactive agents. That is, in addition to relatively small hardy compounds such as steroids, the preparations of the present invention may be formulated to effectively incorporate larger, fragile molecules such as peptides, proteins and genetic material.

EXAMPLE IX

Preparation of Hollow Porous Powder by Spray Drying a Gas-in-Water Emulsion

The following solutions were prepared with water for injection:

Solution 1: 3.9% w/v M-HES hydroxyethylstarch (Ajinomoto, Tokyo, Japan) 3.25% w/v Sodium chloride (Mallinckrodt, St. Louis, Mo.) 2.83% w/v Sodium phosphate, dibasic (Mallinckrodt, St. Louis, Mo.) 0.42% w/v Sodium phosphate, monobasic (Mallinckrodt, St. Louis, Mo.)

Solution 2: 0.45% w/v Poloxamer 188 (BASF, Mount Olive, N.J.) 1.35% w/v Hydrogenated egg phosphatidylcholine, EPC-3 (Lipoid KG, Ludwigshafen, Germany)

The ingredients of solution 1 were dissolved in warm water using a stir plate. The surfactants in solution 2 were dispersed in water using a high shear mixer. The solutions were combined following emulsification and saturated with nitrogen prior to spray drying.

The resulting dry, free flowing, hollow, spherical product had a mean particle diameter of 2.6±1.5 μm. The particles, which may be used for the replacement or augmentation of lung surfactant, were spherical and porous as determined by SEM.

This example illustrates the point that a wide variety of blowing agents (here nitrogen) may be used to provide microstructures exhibiting desired morphology. Indeed, one of the primary advantages of the present invention is the ability to alter formation conditions so as to preserve biological activity (i.e. with proteins or lung surfactant) or produce microstructures having selected porosity.

EXAMPLE X

Preparation of Perforated Microstructure Powder Containing Ampicillin

The following materials were obtained and used to provide a feed stock: 20% w/w Ampicillin, Biotech grade (Fisher Scientific, Pittsburgh, Pa.) 14.38% w/w Hydroxyethyl starch (Ajinomoto, Japan) 65.62% w/w Dipalmitoylphosphatidylcholine (Genzyme, Cambridge, Mass.) Perfluorohexane (3M, St. Paul, Minn.) Deionized water Hydroxyethyl starch, (HES; 0.9 g), and dipalmitoylphosphatidylcholine (DPPC; 4.11 g) were dispersed in 75 ml deionized water using an Ultra-Turrax mixer (model T-25) at 10,000 rpm for approximately 2 minutes (T=45-50.° C.). The resulting DPPC/HES dispersion was chilled in an ice bath. Ampicillin (1.25 g) was added and allowed to mix for 1 minute (T=5-10.° C.). Perfluorohexane (PFH, 4.11 g) was then added dropwise during mixing (T=5-10° C.). After the addition was complete, the PFH-in-water emulsion was mixed on the Ultra-Turrax for a total of not less than 4 minutes.

A perforated microstructure powder comprising ampicillin was obtained by spray-drying (Büchi, 191 Mini Spray Dryer, Switzerland) the ampicillin containing emulsion at a rate of 5.5 ml/min. The inlet and outlet temperatures of the spray dryer were 90° C. and 55° C. respectively. The nebulization air and aspiration flows were 1,800 L/hr and 100% respectively. A free flowing white powder comprising porous microspheres was obtained.

EXAMPLE XI

Preparation of Perforated Microstructure Powder Containing Insulin

The following materials were obtained and used to provide a feed stock: 0.0045% w/w Human Insulin, (Calbiochem, San Diego, Calif.) 17.96% w/w Hydroxyethyl starch (Ajinomoto, Japan) 82.04% w/w Dipalmitoylphosphatidylcholine (Genzyme, Cambridge, Mass.) Perfluorohexane (3M, St. Paul, Minn.) Deionized water Hydroxyethyl starch, (HES; 1.35 g) and dipalmitoylphosphatidylcholine (DPPC; 6.16 g) were dispersed in 100 ml deionized water using an Ultra-Turrax mixer (model T-25) at 10,000 rpm for approximately 2 minutes (T=45-50° C.). The resulting DPPC/HES dispersion was then chilled in an ice bath. Insulin (3.4 mg) was added and allowed to mix for 1 minute (T=5-10° C.). Perfluorohexane (PFH, 6.16 g) was then added dropwise during mixing (T=5-10° C.). After the addition was complete, the resulting PFH-in-water emulsion was mixed with the Ultra-Turrax) for a total of not less than 4 minutes. The insulin microstructure powder was obtained using a Büchi model 191 mini spray dryer (Büchi, Switzerland). The insulin containing emulsion was fed at a rate of 5.5 ml/min. The inlet and outlet temperatures of the spray dryer were 80° C. and 45° C. respectively. The nebulization air and aspiration flows were 1,800 L/hr and 100% respectively. A free flowing, white powder comprising porous microspheres was obtained.

EXAMPLE XII

Preparation of Fluorescent-Labeled Perforated Microstructure Powder via Spray Drying The following materials were obtained and used to manufacture feed stock: 0.2% w/w Nitrobenzoyldiol Phosphatidylcholine (Avanti Polar Lipids, Alabaster, Ala.) 17.6% w/w Hydroxyethyl starch (Ajinomoto, Japan) 82.2% w/w Dipalmitoylphosphatidylcholine (Genzyme, Cambridge, Mass.) Perfluorohexane (3M, St. Paul, Minn.) Deionized water Dipalmitoylphosphatidylcholine (DPPC; 1 g) and nitrobenzoyldiol phosphatidylcholine (NBD-PC; 10 mg) were dissolved in 4 ml chloroform. The chloroform was then removed using a Savant Speed Vac™ (Model SC 200). Hydroxyethyl starch, (RES; 0.9 g), dipalmitoylphosphatidylcholine (DPPC; 3.19 g) and 75 ml deionized water were then added to the DPPC/NBD-PC thin film. The surfactants and starch were then dispersed in the aqueous phase using an Ultra-Turrax mixer (model T-25) at 10,000 rpm for approximately 2 minutes (T=45-50° C.). The resulting NBD-PC/DPPC/HES dispersion was chilled in an ice bath. Perfluorohexane (PFH, 4.11 g ) was then added dropwise during mixing (T=5-10° C.). After the addition was complete, the resulting PFH-in-water emulsion was mixed on the Ultra-Turrax for an additional time of not less than 4 minutes. The fluorescently labeled microshell powder was obtained by spray drying (Büchi, 191 Mini Spray Dryer, Switzerland). The NBD-PC/DPPC/HES containing emulsion was fed at a rate of 5.5 ml/min. The inlet and outlet temperatures of the spray dryer were 100° C. and 65° C. respectively. The nebulization air and aspiration flows were 1,800 L/hr and 100% respectively. A free flowing, yellow powder comprising perforated microstructures was obtained.

EXAMPLE XIII

Effect of Spray Drying on the In-Vitro Activity of Lung Surfactant

The activity of a spray dried lung surfactant preparation to lower the surface tension of a pulsating bubble was compared with the neat lung surfactant preparation. Bovine derived lung surfactant, Alveofact (Thomae, Biberach, Germany) and spray-dried lung surfactant containing microshells were dissolved in normal saline at a concentration of 10 mg/ml and allowed to incubate for 15 minutes at 37° C. Prior to analysis, the surfactant test solutions were vigorously shaken using a Vortex mixer for 30 seconds. The samples were analyzed for their surface properties using the Pulsating Bubble Surfactometer at 37° C. (model EC-PBS-B, Electronics, Amherst, N.Y.) according to the manufacturers instructions. Surfactant solutions were allowed to adsorb at minimum bubble diameter for 10 seconds, and bubble cycling was performed in the automatic mode (20 cycles/minute). For each experiment, measurements were taken for approximately the first 10 cycles, then again at 2, 4, and 6 minutes.

The main difference observed between the neat and spray dried surfactant suspensions is the rate at which they adsorb to the bubble surface and thus lower the tension. The spray-dried materials required 6 cycles to achieve low surface tension as compared with one cycle for the Alveofact sample. However, the magnitude of the tension at maximum, and minimum bubble diameter were found to be approximately the same.

For the Alveofact dispersion, the tension decreased from 32 mN/m at maximum diameter to 4 mN/m at minimum in the first cycle. With further pulsation, a steady state oscillation was reached with a maximum tension $\gamma_{max}\approx 33$ mN/m and a minimum tension $\gamma_{min}\approx 0$ to 1 mN/m. For the spray-dried lung microshell dispersion, the tension decreased from 36 mN/m at maximum diameter to 16 mN/m at minimum in the first cycle. By the sixth pulsation, $\gamma_{max}$ and $\gamma_{min}$ were respectively 36 and 2 mN/m. Both the neat Alveofact and the spray-dried lung surfactant perforated microstructures satisfy the maximum and minimum surface tension requirements for physiologically effective lung surfactants as outlined by Notter; [R. H. Notter, in Surfactant Replacement Therapy, (Eds: D. H. Shapiro, and R. H. Notter) Alan R. Liss, New York, 1989] these values should range from 35 to about 5 mN/m, respectively. This example illustrates that, the compositions and methods of the present invention are particularly useful for the replacement or augmentation of lung surfactant in patients.

EXAMPLE XIV

Rapid Spreading of Spray-Dried Microshells in PFC's

Stabilized dispersions formed according to the present invention provide for enhanced surfactant spreading at the pulmonary air/water interface. In this regard, the equilibrium surface tension of dimyristoylphosphatidylcholine is ca. 22 mN/m. Aqueous based liposomes are adsorbed very slowly at the air/water interface as evidenced by the fact that, after 1800 seconds, the surface tension of an aqueous solution has not been significantly reduced. The slow adsorption for liposomes is due to the slow molecular diffusion of DMPC through the water phase. Surprisingly, adsorption of DMPC suspended in perflubron (PFOB) in the form of dry perforated microstructures is very fast, reducing the surface tension to equilibrium values within a few seconds. This rapid spreading and reduction of surface tension is indicative of what would occur upon contacting the perforated microstructures with a wetted pulmonary membrane. More specifically, the present example demonstrates that the disclosed stabilized dispersions provide for the effective delivery of lung surfactants, and drugs to the lung by liquid dose instillation.

EXAMPLE XV

Pharmacokinetics for Insulin and Glucose Following Administration via LDI vs. IM The insulin formulation described in Example XI was administered via liquid dose instillation (0.86 IU in 4.5 ml/kg of perflubron) and intramuscular (IM) to fasting rabbits. In the case of LDI administration, rabbits were anesthetized, intubated, placed on a respirator, and their lungs were instilled with ca. 4.5 ml/kg of perflubron. The hollow porous microsphere formulation of insulin was then top-loaded in a minimal perflubron volume onto the existing perflubron in the lung, at a dose of 0.86 IU/kg. Control animals were injected IM with a similar dose of insulin (Humulin R). Plasma levels of insulin were determined by a radioimmunoassay method, and the decrease in serum glucose levels were also determined. The results are shown in Tables III and IV. Extremely fast uptake of insulin into the systemic circulation was observerd following LDI administration. The relative bioavailability was found to be 53% Little differences were noted in glucose modulation between the IM and LDI groups. These results show the utility of LDI administration in the systemic delivery of bioactive agents.

TABLE III

Insulin Pharmacokinetics following LDI or IM administration to rabbits

| Delivery Mode | $C_{max}$ (μU/ml) | $T_{max}$ (min.) | AUC (μU min/ml) | $B_{IM}$ (%) |
|---|---|---|---|---|
| IM | 110.5 | 60 | 20770 | 100 |
| LDI (4.5 ml/kg) | 210.4 | 15 | 11100 | 53 |

TABLE IV

Serum glucose levels (mg/dl) following LDI or IM administration to rabbits

| Time (min.) | IM | LDI |
|---|---|---|
| 0 | 184.2 | 175.7 |
| 5 | 253.6 | 218.8 |
| 10 | 256.0 | 211.7 |
| 15 | 216.8 | 198.2 |
| 30 | 168.2 | 143.3 |
| 60 | 82.0 | 83.2 |
| 90 | 48.2 | 38.2 |
| 120 | 18.0 | 31.2 |
| 150 | 29.4 | 31.7 |
| 180 | 28.8 | 33.4 |
| 240 | 29.4 | 49.2 |
| 360 | 115.8 | — |

EXAMPLE XVI

Reduction in Rat Mortality Following Liquid Dose Instillation of Antibiotics

Male Wistar rats (ca 500 g) were inoculated intratracheally with $10^9$ colony forming units of Streptococcus pneumoniae. The model is an acute pneumonia model with 100% of untreated control animals within 4 days of inoculation. Animals receiving 10 mg of ampicillin intramuscularly one day after inoculation exhibited improved survival with 27% of the animals surviving to 10 days. Animals receiving 10 mg of ampicillin (prepared according to Example X) in 10 ml of perflubron via LDI administration exhibited a survival of 87%. These results indicate that local antibiotic treatment with the hollow porous microspheres of the present invention, is extremely efficient in reducing the mortality associated with life-threatening bacterial infections.

EXAMPLE XVII

Ampicillin Concentrations in the Lung and Serum Following IM and LDI Administration Ampicillin concentrations in lung tissue and serum were measured for the two treatment groups in Example XV by a bioassay method. In this method, 60 μl of lung tissue homogenate, or serum obtained from the rats at various points after dosing is placed on a sterile disk. The disk is then placed on an agar plate covered with *S. pneumoniae* and incubated for 24 hr. Levels of antibiotic high enough to inhibit growth of *S. pneumoniae* resulted in zones of growth inhibition around the disk. The no-growth zones were quantitated, and concentrations of antibiotic were calculated based on a standard curve.

The results for the IM and LDI groups are shown in Table V. Ampicillin has a short half-life in serum as noted by the fact that ampicillin levels are undetectable following IM administration after only 2 hours. Following LDI administration, the serum levels persisted for at least 4 hours, indicating a sustained release of ampicillin into the blood. Similarly, the local lung concentrations were 250 times higher with LDI delivery and persisted for several days. These results indicate that large local antibiotic concentrations can be achieved at the site of the infection, without correspondingly high serum levels, following LDI administration. Moreover, unlike intramuscular administration, the higher concentrations provided by liquid dose instillation also persisted for several days following administration. Such persistence could significaly reduce dosing requirements.

TABLE V

Ampicillin pharmacokinetics in rat lung: effect of mode of administration.

| Time (hr) | IM serum | IM lung | LDI serum | LDI lung |
|---|---|---|---|---|
| 1 | 15.0 | 2.2 | 15.8 | 501.2 |
| 2 | 1.3 | 1.2 | 2.0 | 125.9 |
| 3 | 0 | 0 | 1.3 | 125.9 |
| 4 | 0 | 0 | 2.5 | 50.1 |
| 8 | 0 | 0 | 0 | 15.8 |
| 24 | 0 | 0 | 0 | 10.0 |
| 48 | 0 | 0 | 0 | 3.0 |
| 72 | 0 | 0 | 0 | 2.0 |

EXAMPLE XVIII

Gentamicin Biodistribution in Rabbit Lung

Comparison of biodistribution in New Zealand white rabbits at one hour post-administration of 5 mg/kg gentamicin by either IM or LDI methods was performed. The gentamicin was administered in an LDI volume of only 1.8 ml/kg. individual lobes of the lungs were collected and analyzed quantitatively for gentamicin by an immunoassay method. The results are detailed in Table VI. The lung gentamicin concentrations were ca. 2 orders of magnitude higher following local administration (LDI) than for IM administration. Excellent biodistribution across the lung lobes was observed following either IM or LDI administration.

TABLE VI

Biodistribution of Gentamicin (μg gentamicin/g tissue) in Rabbit Lungs Following LDI and IM Administration

| Administration Mode | Right Upper | Right Mid | Right Lower | Left Upper | Left Lower |
|---|---|---|---|---|---|
| IM | 5.0 | 6.0 | 6.4 | 6.7 | 6.1 |
| LDI | 680.5 | 564.3 | 646.7 | 206.3 | 412.9 |

Those skilled in the art will further appreciate that the present invention may be embodied in other specific forms without departing from the spirit or central attributes thereof In that the foregoing description of the present invention discloses only exemplary embodiments thereof, it is to be understood that, other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. A dispersion for the pulmonary delivery of a bioactive agent to a patient, the dispersion comprising:

(a) a plurality of permeable microstructures, the permeable microstructures comprising at least one bioactive agent, and (b) a suspension medium that permeates into the permeable microstructures.

2. A dispersion according to claim 1 wherein the permeable microstructures comprise at least one of a phospholipid, nonionic detergent, nonionic block copolymer, ionic surfactant, biocompatible fluorinated surfactant or combinations thereof.

3. A dispersion according to claim 1 wherein the permeable microstructures comprise a phospholipid.

4. A dispersion according to claim 3 wherein the phospholipid is a saturated phospholipid.

5. A dispersion according to claim 3 wherein the permeable microstructures comprise an inorganic salt.

6. A dispersion according to claim 5 wherein the inorganic salt comprises calcium chloride.

7. A dispersion according to claim 5 wherein the gel to liquid transition temperature of the permeable microstructures is greater than 40° C.

8. A dispersion according to claim 1 wherein the permeable microstructures and suspension medium have a refractive index differential of less than 0.5.

9. A dispersion according to claim 1 wherein the permeable microstructures have a mean density selected to provide a density differential with that of the suspension medium of less than 0.6 g/cm$^3$.

10. A dispersion according to claim 1 wherein the suspension medium comprises a fluorochemical.

11. A dispersion according to claim 1 wherein the bioactive agent comprises one or more of antiallergics, bronchodilators, pulmonary lung surfactants, analgesics, antibiotics, leukotriene inhibitors or antagonists, antihistamines, anti-inflammatories, antineoplastics, anticholinergics, anesthetics, anti-tuberculars, imaging agents, cardiovascular agents, enzymes, steroids, genetic material, viral vectors, antisense agents, proteins, peptides or combinations thereof.

12. A dispersion according to claim 1 wherein the bioactive agent is gentamicin.

13. A dispersion according to claim 1 wherein the permeable microstructures have a mean diameter of 1-30 μm.

14. A dispersion for the pulmonary delivery of a bioactive agent to a patient, the dispersion comprising:

(a) a plurality of permeable microstructures, the permeable microstructures comprising at least one of a phospholipid, nonionic detergent, nonionic block copolymer, ionic surfactant, biocompatible fluorinated surfactant or combinations thereof;

(b) at least one bioactive agent; and (c) a suspension medium that permeates into the permeable microstructures.

15. A dispersion according to claim 14 wherein the permeable microstructures comprise a phospholipid.

16. A dispersion according to claim 15 wherein the phospholipid is a saturated phospholipid.

17. A dispersion according to claim 14 wherein the permeable microstructures comprise an inorganic salt.

18. A dispersion according to claim 17 wherein the inorganic salt comprises calcium chloride.

19. A dispersion according to claim 17 wherein the gel to liquid transition temperature of the permeable microstructures is greater than 40° C.

20. A dispersion according to claim 17 wherein the permeable microstructures and suspension medium have at least one of:

(1) a refractive index differential of less than 0.5; or (2) a density differential of less than 0.6 g/$cm^3$.

21. A dispersion according to claim 14 wherein the bioactive agent comprises one or more of antiallergics, bronchodilators, pulmonary lung surfactants, analgesics, antibiotics, leukotriene inhibitors or antagonists, antihistamines, antiinflammatories, antineoplastics, anticholinergics, anesthetics, anti-tuberculars, imaging agents, cardiovascular agents, enzymes, steroids, genetic material, viral vectors, antisense agents, proteins, peptides or combinations thereof.

* * * * *